US007247288B2

(12) United States Patent
Kumta et al.

(10) Patent No.: US 7,247,288 B2
(45) Date of Patent: Jul. 24, 2007

(54) METHOD OF MANUFACTURING HYDROXYAPATITE AND USES THEREFOR IN DELIVERY OF NUCLEIC ACIDS

(75) Inventors: Prashant N. Kumta, Pittsburgh, PA (US); Charles Sfeir, Pittsburgh, PA (US); Jeffrey Hollinger, Pittsburgh, PA (US); Daiwon Choi, Pittsburgh, PA (US); Lee Weiss, Pittsburgh, PA (US); Phil Campbell, Cranberry Township, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 479 days.

(21) Appl. No.: 10/393,507

(22) Filed: Mar. 19, 2003

(65) Prior Publication Data

US 2003/0219466 A1 Nov. 27, 2003

Related U.S. Application Data

(60) Provisional application No. 60/373,494, filed on Apr. 18, 2002.

(51) Int. Cl.
*C01B 25/12* (2006.01)
*A61L 27/32* (2006.01)
*A61F 2/00* (2006.01)
*A61K 31/715* (2006.01)

(52) U.S. Cl. .................. 423/308; 427/2.27; 424/423; 514/44

(58) Field of Classification Search .................. None
See application file for complete search history.

(56) References Cited

U.S. PATENT DOCUMENTS

| | | | |
|---|---|---|---|
| 5,122,418 A * | 6/1992 | Nakane et al. ............ 424/401 |
| 5,128,169 A * | 7/1992 | Saita et al. ............ 427/2.27 |
| 5,258,044 A | 11/1993 | Lee | |
| 5,292,253 A * | 3/1994 | Levy ............ 433/215 |
| 5,306,305 A | 4/1994 | Lee | |
| 5,441,739 A | 8/1995 | Kossovsky et al. | |
| 5,460,830 A | 10/1995 | Kossovsky et al. | |
| 5,460,831 A | 10/1995 | Kossovsky et al. | |
| 5,462,750 A | 10/1995 | Kossovsky et al. | |
| 5,462,751 A | 10/1995 | Kossovsky et al. | |
| 5,464,634 A | 11/1995 | Kossovsky et al. | |
| 5,543,019 A | 8/1996 | Lee et al. | |
| 5,639,505 A | 6/1997 | Kossovsky et al. | |
| 5,650,176 A | 7/1997 | Lee et al. | |
| 5,676,976 A | 10/1997 | Lee et al. | |
| 5,683,461 A | 11/1997 | Lee et al. | |
| 5,763,416 A * | 6/1998 | Bonadio et al. ............ 514/44 |
| 5,776,193 A * | 7/1998 | Kwan et al. ............ 424/423 |
| 5,783,217 A | 7/1998 | Lee et al. | |
| 5,843,289 A | 12/1998 | Lee et al. | |
| 5,858,318 A * | 1/1999 | Luo ............ 423/308 |
| 5,919,426 A * | 7/1999 | Nakamoto et al. ............ 423/308 |
| 6,013,591 A * | 1/2000 | Ying et al. ............ 501/1 |
| 6,027,742 A | 2/2000 | Lee et al. | |
| 6,033,582 A | 3/2000 | Lee et al. | |
| 6,117,456 A | 9/2000 | Lee et al. | |
| 6,132,463 A | 10/2000 | Lee et al. | |
| 6,171,610 B1 | 1/2001 | Vacanti et al. | |
| 6,177,273 B1 | 1/2001 | Bennett et al. | |
| 6,214,368 B1 | 4/2001 | Lee et al. | |
| 6,309,635 B1 | 10/2001 | Ingber et al. | |
| 6,348,069 B1 | 2/2002 | Vacanti et al. | |
| 6,562,069 B2 * | 5/2003 | Cai et al. ............ 623/2.12 |
| 2002/0173478 A1 | 11/2002 | Gewirtz | |

FOREIGN PATENT DOCUMENTS

WO    WO 01/91848 A2    12/2001
WO    WO 02/02182 A2    1/2002

OTHER PUBLICATIONS

Watson, James D., Gilman, Michael, Witkowski, Jan, and Zoller, Mark, "Transferring Genes Into Mammalian Cells," *Recombinant DNA*, 2nd ed., pp. 213-234, W. H. Freeman and Company, New York (1992).

Bonadio, Jeffrey, Smiley, Elizabeth, Patil, Pravin and Goldstein, Steven, "Localized, direct plasmid gene delivery in vivo; prolonged therapy results in reproducible tissue regeneration," *Nature Medicine*, vol. 5, No. 7, pp. 753-759, (1999).

Xia, Haibin, Mao, Qinwen, Paulson, Henry L. and Davidson, Beverly L., "siRNA-mediated gene silencing in vitro and in vivo," *Nature Biotechnology*, vol. 20, pp. 1006-1010, (2002).

Amrani, David L., Diorio, James P. and Delmotte, Yves, "Wound Healing: Role of Commercial Fibrin Sealants," *Annals New York Academy of Sciences*, pp. 566-579.

Hollinger, Jeffrey O., Brekke, John, Gruskin, Elliott and Lee, Dosuk, "Role of Bone Substitutes," *Clinical Orthopaedics and Related Research*, No. 324, pp. 55-65 (1996)/.

Nakashima, M., The Effects of Growth Factors on DNA Synthesis, Proteoglycan Synthesis and Alkaline Phosphatase Activity in Bovine Dental Pulp Cells, *Archs oral Biol.*, vol. 37, No. 3, pp. 231-236 (1992).

Lasa, Carlos Jr., Hollinger, Jeffrey, Drohan, William and MacPhee, Martin, "Delivery of Demineralized Bone Powder by Fibrin Sealant," *Plastic and Reconstructive Surgery*, vol. 96, No. 6, pp. 1409-1417 (1995).

(Continued)

*Primary Examiner*—Richard Schnizer
(74) *Attorney, Agent, or Firm*—Kirkpatrick & Lockhart Preston Gates Ellis LLP

(57) ABSTRACT

Provided is a method for production of nanocrystalline hydroxyapatite particles, and nanocrystalline hydroxyapatite particles produced according to the method. The nanocrystalline hydroxyapatite particles exhibit substantially superior cell transformation abilities as compared to known and commercially-available calcium phosphate kits. The nanocrystalline hydroxyapatite particles also find use in tissue engineering applications, for example bone and tooth engineering and repair applications.

34 Claims, 19 Drawing Sheets

OTHER PUBLICATIONS

Bolander, Mark E., Regulation of Fracture Repair by Growth Factors (43410A), *Proceedings of the Society for Experimental Biology and Medicine*, pp. 165-170, (1992).

Bègue-Kirin, Catherine, Smith, Anthony J., Ruch, Jean Victor et al., "Effects of dentin proteins, transforming growth factor β1 (TGFβ1) and bone morphogenetic protein 2 (CMP2) on the differentiation of odontoblast in vitro," *Int. J. Dev. Biol.*, 36: 491-503 (1992).

Imai, M. and Hayashi, Y., "Ultrastructure of wound healing following direct pulp capping with calcium-β-glycerophosphate (Ca-BGP)," *J. Oral Pathol Med*: 22; 411-417 (1993).

Abstract: Ren, Wen Hong, Yang, Lian Jia and Dong, Shao Zhong, "Induction of Reparative Dentin Formation in Dogs with Combined Recombinant Human Bone Morphogenetic Protein 2 and Fibrin Sealant," *Chinese Journal of Dental Research*, vol. 2:3:21-24 (1999).

Carr, M.E. Jr. and Alving, B.M., "Effect of fibrin structure on plasmin-mediated dissolution of plasma clots," *Blood Coagulation and Fibrinolysis*, vol. 6, pp. 567-573 (1995).

Hu, Y., Hollinger, J.O. and Marra, K.G., "Controlled Release from Coated Polymer Microparticles Embedded in Tissue-engineered Scaffolds," *Journal of Drug Targeting*, vol. 9, pp. 431-438, (2001).

Hollinger, J., Mayer, M., Buck, D., Zegzula, H., et al., "Poly (α-hydroxy acid) carrier for delivering recombinant human bone morphogenetic protein-2 for bone regeneration," *Journal of Controlled Release*, 39, pp. 287-304 (1996).

Abe, Nobuhiro, Lee, Yu-Po, Sato, Makoto, Zhang, Xuguang, et al., "Enhancement of bone repair with a helper-dependent adenoviral transfer of bone morphogenetic protein-2," *Biochemical and Biophysical Research Communications*, vol. 297, pp. 523-527 (2002).

Davis, Sean E., Doss, David J., Humphrey, Jay D. and Wright, T. Neil, "Effects of Heat-Induced Damage on the Radial Component of Thermal Diffusivity of Bovine Aorta," *Journal of Biomechanical Engineering*, vol. 122, pp. 283-285 (2000).

Oldham, J.B., Lu, L., Zhu, X. and Porter, B.D. et al., "Biological Activity of rhBMP-2 Released from PLGA Microspheres," *Journal of Biomechanical Engineering*, vol. 122, pp. 289-292 (2000).

Porter, B.D., Oldham, J.B., He, S.-L. and Zobitz, M.E. et al., "Mechanical Properties of a Biodegradable Bone Regeneration Scaffold," *Journal of Biomechanical Engineering*, vol. 122, pp. 286-288 (2000).

Ren, Wen Hong, Yang, Lian Jia and Dong, Shao Zhong, "Induction of Reparative Dentin Formation in Dogs with Combined Recombinant Human Bone Morphogenetic Protein 2 and Fibrin Sealant," *The Chinese Journal of Dental Research*, vol. 2, No. 3/4, pp. 21-24 (1999).

Ikoma, Toshiyuki, Yamazaki, Atushi, Nakamura, Satoshi and Akao, Masaru, "Preparation and Structure Refinement of Monoclinic Hydroxyapatite," *Journal of Solid State Chemistry*, vol. 144, 272-276 (1999).

Nowotny, R., Chalupka, A., Nowotny, Ch. and Bosch, P., "Preparation of fibrin clot samples for tensile stress-strain experiments," *Biomaterials*, vol. 2, pp. 55-56 (1981).

Wigler, Michael, Pellicer, Angel, Silverstein, Saul and Axel, Richard, "Biochemical Transfer of Single-Copy Eucaryotic Genes Using Total Cellular DNA as Donor," *Cell.*, vol. 14, pp. 725-731 (1978).

Graham, F.L. and Van Der Eb, A.J., "Transformation of Rat Cells by DNA of Human Adenovirus," *Virology*, vol. 54, pp. 536-639 (1973).

Toriyama, Motohiro, Kawamoto, Yukari, Suzuki, Takahiro et al., "Synthesis of Hydroxyapatite by an Oxidative Decomposition Method of Calcium Chelate," *Journal of the Ceramic Society of Japan. Int. Edition*, vol. 100, pp. 939-943 (1992).

Zawa, T.Kana, "Hydroxyapatite," in Inorganic Phosphate Materials, *Materials Science Monographs*, vol. 52, pp. 15-54 (1989).

Doremus, R.H., "Review Bioceramics," *Journal of Materials Science*, vol. 27, pp. 285-297 (1992).

Hu, C.-C., Zhang, Chuhua, Qian, Qiubing and Tatum, Nanni B., "Reparative Dentin Formation in Rat Molars after Direct Pulp Capping with Growth Factors," *Journal of Endodontics*, vol. 24, No. 11, pp. 744-751 (1998).

Spitzer, Ron-Sascha, Perka, Carsten, Lindenhayn, Klaus and Zippel, Hartmut, "Matrix engineering for osteogenic differentiation of rabbit periosteal cells using α-tricalcium phosphate particles in a three-dimensional fibrin culture," *J. Biomed. Mater. Res.*, pp. 690-696, (2002).

Nakashima, M., "The Induction of Reparative Dentine in the Amputated Dental Pulp of the Dog by Bone Morphogenetic Protein," *Archs oral Biol.*, vol. 35, No. 7, pp. 493-497, (1990).

Rutherford, B., "Dentin Regeneration," *Adv. Dent. Res.*, 9(3)(Suppl.):14, (1995).

Rutherford, B., Spängbert, L., Tucker, M., Rueger, D., and Charette, M., "The Time-Course of the Induction of Reparative Dentine Formation in Monkeys by Recombinant Human Osteogenic Protein-1," *Archs oral Biol.*, vol. 39, No. 10, pp. 833-838, (1994).

Heys, D.R., Fitzgerald, M., Heys, R.J. and Chiego, D.J., "Healing of primate dental pulps capped with Teflon," *Oral Surg Oral Med Oral Pathol*, vol. 69, pp. 227-237 (1990).

Lee, A.N., Zhang, S.M., Wu, J., Lieberman, M.K., "Enhancement of bone repair with a helper-dependent adenovira transfer of bone morphogenetic protein-2," *Biochem Biophys Res Commun.*, vol. 297(3), pp. 523-227 (2002) (abstract only).

Rutherford, R.B., Wahle, J., Tucker, M., Rueger, D. and Charette, M., "Induction of Reparative Dentine Formation in Monkeys by Recombinant Human Osteogenic Protein-1," *Archs oral Biol.*, vol. 38, No. 7, pp. 571-576 (1993).

Whang, K., Tsai, D.C., Nam, E.K., Aitken, M., Sprague, S.M., Patel, P.K. and Healy, K.E., "Ectopic bone formation via rhBMP-2 delivery from porous bioabsorbable polymer scaffolds," *J Biomed Mater Res*, vol. 42, pp. 491-499 (1998).

Zegzula, D.H., Buck, D.C., Brekke, J., Wozney, J.M. and Hollinger, J.O., "Bone Formation with Use of rhBMP-2 (Recombinant Human Bone Morphogenetic Protein-2)," *J Bone Joint Surg Am*, vol. 79-A(12), pp. 1778-1790 (1997).

Urist, M.R., "Bone: Formation by Autoinduction," *Science*, New Series, vol. 150, No. 3698, pp. 893-899 (1965).

Uludag, H., D'Augusta, D., Golden, J., Li, J., Timony, G., Riedel, R. and Wozney, J.M., "Implantation of recombinant human bone morphogenetic proteins with biomaterial carriers: A correlation between protein pharmacokinetics and osteoinduction in the rat ectopic model," *J. Biomed Mater Res*, vol. 50, pp. 227-238 (2000).

Barnes, G.L., Kostenuik, P.J., Gerstenfeld, L.C. and Einhorn, Thomas A., "Perspective: Growth Factor Regulation of Fracture Repair," *Journal of Bone and Mineral Research*, vol. 14, No. 11, pp. 1805-1815 (1999).

Uludag, H., D'Agusta, D., Palmer, R., Timony, G. and Wozney, J., "Characterization of rhBMP-2 pharmacokinetics implanted with biomaterial carriers in the rat ectopic model," *J Biomed Mater Res*, vol. 46, pp. 193-202 (1999).

Reddi, A.H., "Initiation of Fracture Repair by Bone Morphogenetic Proteins," *Clin Orthop*, vol. (355S) Supplemental, pp. S-66-S72 (1998).

Ogawa, Yasushi, Schmidt, D.K., Nathan, R.M., Armstrong, R.M., Miller, K.L. et al., "Bovine Bone Activin Enhances Bone Morphogenetic Protein-induced Ectopic Bone Formation," *The Journal of Biological Chemistry*, vol. 267, No. 20, pp. 14233-14237 (1992).

Nakashima, M., Nagasawa, H., Yamada, Y. and Debbi, H., "Regulatory Role of Transforming Growth Factor-β , Bone Morphogenetic Protein-2, and Protein-4 on Gene Expression of Extracellular Matrix Proteins and Differentiation of Dental Pulp Cells," *Developmental Biology*, vol. 162, pp. 18-28 (1994).

Marra, K.G., Szem, J.W., Kumta, P.N., DiMilla, P.A. and Weiss, L.E., "In vitro analysis of biodegradable polymer blend/hydroxyapatite composites for bone tissue engineering," *J Biomed Mater Res*, vol. 47, pp. 324-335 (1999).

Lu, H.H., El-Amin, S.F., Scott, K.D. and Laurencin, C.T., "Three-dimensional, bioactive, biodegradable, polymer-bioactive glass composite scaffolds with improved mechanical properties support collagen synthesis and mineralization of human osteoblast-like cells in vitro," *J. Biomed Mater Res*, vol. 64A, pp. 465-474 (2003).

Lee, J.Y., Peng, H., Usas, A., Musgrave, D., Cummins, J., et al., "Enhancement of Bone Healing Based on Ex Vivo Gene Therapy Using Human Muscle-Derived Cells Expresssing Bone Morphogenetic Protein 2," *Human Gene Therapy*, vol. 13, pp. 1201-1211 (2002).

Laurencin, C.T., Attawia, M.A., Lu, L.Q., Borden, M.D., Lu, H.H., Gorum, W.J. and Lieberman, J.R., "Poly(lactide-co-glycolide)hydroxyapatite delivery of BMP-2-producing cells: a regional gene therapy to bone regeneration," *Biomaterials*, vol. 22, pp. 1271-1277 (2001).

Krebsbach, P.H., Gu, K., Franceschi, R.T. and Rutherford, R.B., Gene Therapy-DirectedOsteogenesis: BMP-7-Transduced Human Fibroblasts From Bone in Vivo, *Human Gene Therapy*, vol. 11, pp. 1201-1210 (2000).

Hollinger, J.O. and Leong, K., "Poly( -hydroxy acids): carriers for bone morphogenetic proteins," *Biomaterials*, vol. 17, pp. 187-194 (1996).

Franceschi, R.T., Wang, D., Krebsbach, P.H. and Rutherford, R.B., "Gene Therapy for Bone Formation: In Vitro and In Vivo Osteogenic Activity of an Adenovirus Expressing BMP7," *Journal of Cellular Biochemistry*, vol. 78, pp. 476-486 (2000).

Fang, J., Zhu,Y-Y., Smiley, E., Bonadio, J., Rouleau, J.P., Goldstein, S.A., et al., "Stimulation of new bone formation by direct transfer of osteogenic plasmid genes," *Proc. Natl. Acad. Sci. USA*, vol. 93, pp. 5753-5758 (1996).

Elbashir, S.M., Harborth, J., Weber, K. and Tuschi, T., "Analysis of gene function in somatic mammalian cells using small interfering RNAs," *Methods*, vol. 26, pp. 199-213 (2002).

Bonadio, J., "Tissue engineering via local gene delivery," *J Mol Med*, vol. 78, pp. 303-311 (2000).

\* cited by examiner

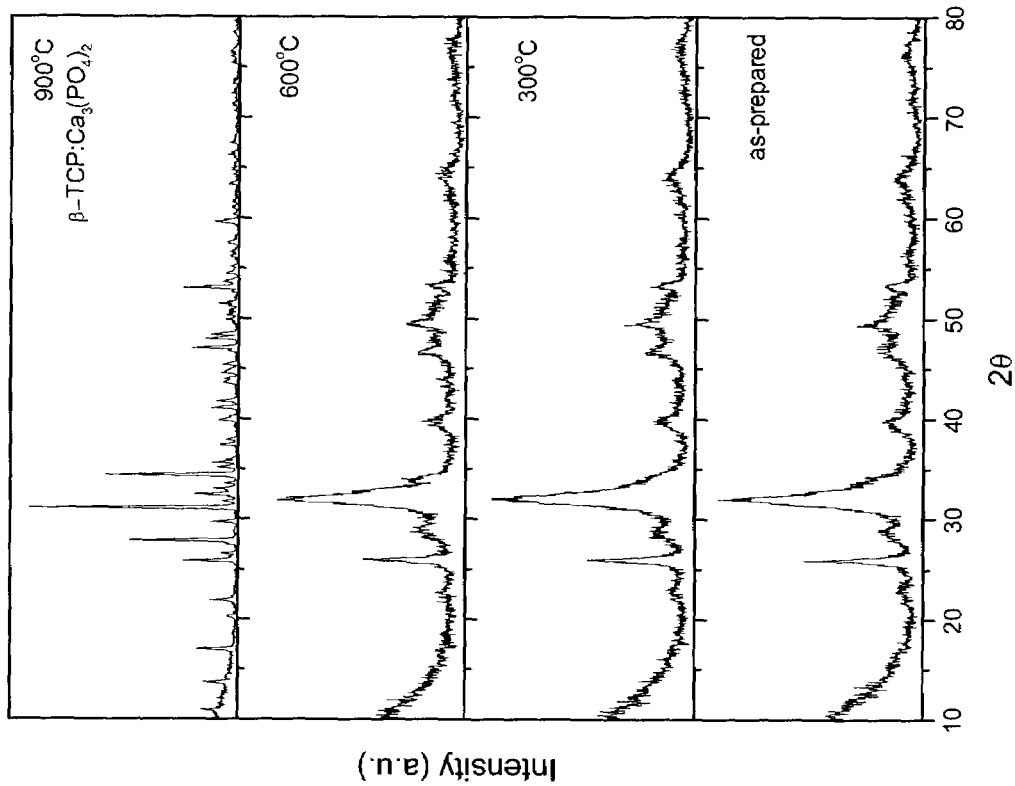
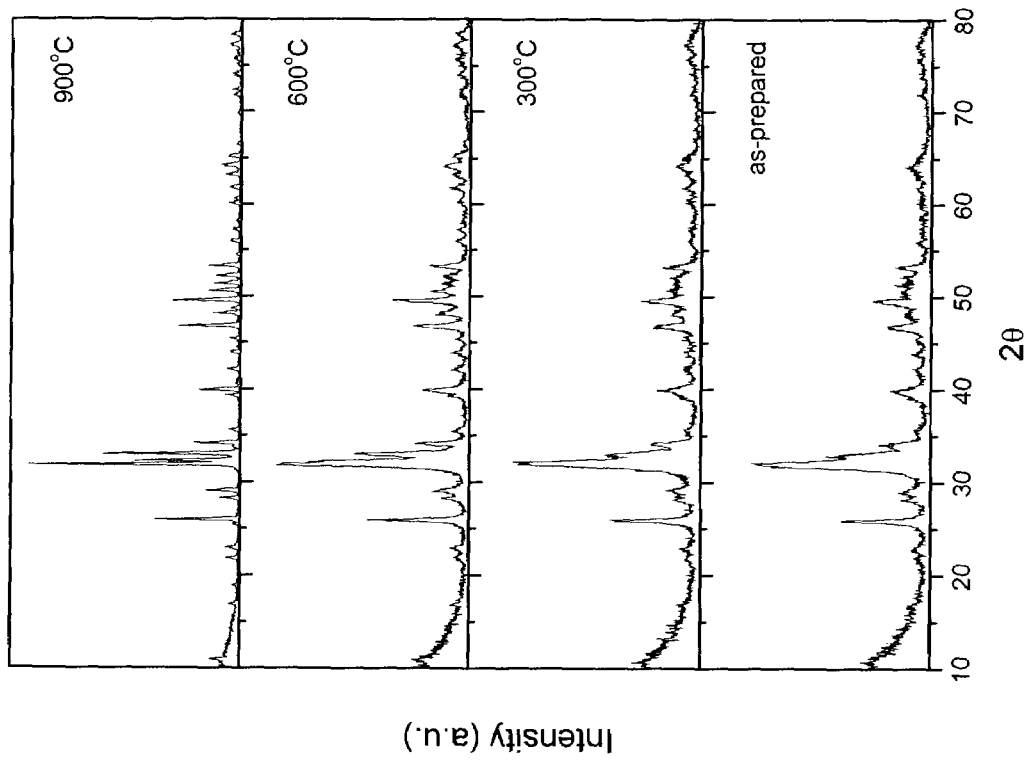
Fig. 3A
Fig. 3B

METHOD OF MANUFACTURING HYDROXYAPATITE AND USES THEREFOR IN DELIVERY OF NUCLEIC ACIDS

CROSS REFERENCE TO RELATED APPLICATIONS

This application claims priority under 35 U.S.C. section 119(e) to U.S. Provisional Patent Application No. 60/373,494, filed Apr. 18, 2002, which is incorporated herein by reference in its entirety.

STATEMENT REGARDING FEDERALLY SPONSORED RESEARCH OR DEVELOPMENT

Not Applicable

BACKGROUND

1. Field of the Invention

Provided is a method for preparing hydroxyapatite, and uses therefor, including in tissue engineering and repair and in gene delivery.

2. Description of the Related Art

Calcium phosphate in its broadest sense is a ubiquitous material that naturally exists in a broad variety of places. It is typically an organic product that is found in bone, teeth and shells of a large variety of animals. It exists in a variety of forms as are well-known in the art, such as hydroxyapatite (Hydroxyapatite, $Ca_{10}(PO_4)_6(OH)_2$, Ca/P=1.67), tricalcium phosphate (TCP, $Ca_3(PO_4)_2$, Ca/P=1.5) and brushite ($CaHPO_4.2H_2O$, Ca/P=1), as well as in amorphous form (ACP, $Ca_x(PO_4)_y.NH_2O$) (Ca/P=~1.5). The relative stability of the predominant forms of calcium phosphate are:

ACP<TCP<<Hydroxyapatite.

Calcium phosphate, in the form of hydroxyapatite has been widely studied as a bone substitute due to its osteoconductive characteristics and its structural similarity to the mineralized matrix of natural bone (T. Kanazawa, *Inorganic phosphate materials*, 1989, 52, p15–20). Hydroxyapatite also has attracted much attention as a substitute material for damaged teeth over the past several decades and its biocompatibility has been experimentally proven to be superior to many other materials.

Nano-structured hydroxyapatite is believed to have several advantages in its use in bone tissue engineering due to its higher surface area and consequently higher reactivity which offers better cellular response. In addition, nano-sized hydroxyapatite is useful as an effective surface modification agent for binding numerous biological molecules.

There are several reported methods for the synthesis of hydroxyapatite. Some of the widely used processes include aqueous colloidal precipitation, sol-gel, solid-state and mechano-chemical methods. The solid state methods require elevated temperatures, which lead to grain growth and coarsening of the microstructure. Low temperature methods such as sol-gel, mechano-chemical synthesis and colloidal precipitation are performed at ambient temperatures and therefore provide the ability to synthesize nano-structured material with direct control of the particle and grain size.

Most widely used aqueous colloidal precipitation reactions to synthesize hydroxyapatite are as follows (R. Doremus. Review Bioceramics, *Journal of Materials Science*, 1992, 27, p285–297):

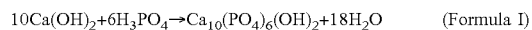

(Formula I)

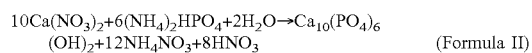

(Formula II)

Current popular methods of gene delivery include viral gene delivery, chemical methods, such as calcium phosphate precipitation methods and liposome delivery. Non-viral plasmid gene delivery methods have certain advantages, including transient expression of the delivered gene, low systemic toxicity and are typically relatively simple to manufacture. However, there procedures typically result in low transfection efficiency. Calcium phosphate has long been recognized as a useful transfection agent, with many commercially available kits (Graham, F. L., et al. (1973); Wigler, M., et al., (1978)). Both of the reactions shown in Formulas I and II require the continuous maintenance of pH in excess of 11.0 during the entire duration (at least 12–24 hours of the reaction) to ensure the formation of stoichiometric quantities of hydroxyapatite. This is a major disadvantage for gene delivery. Furthermore this pH range is not suitable for cell stability and growth. Therefore, there is a need for a much more effective and a biocompatible synthesis approach.

Gene delivery recently has been investigated for use in bone tissue engineering therapies to repair or heal challenging wound or defect sites. Tissue engineering approaches have typically involved implanting 3D biomimetic extracellular matrices (bECMs), seeded with cells or signaling molecules (SMs) or both, into defects to induce and guide the growth of new bone by host tissue ingrowth (Oldham, J. B., et al., "Biological activity of rhBMP-2 released from PLGA microspheres," *J Biomech Eng*. 2000 June;122(3): 289–92; Whang, K., et al., "Ectopic bone formation via rhBMP-2 delivery from porous bioabsorbable polymer scaffolds." *J Biomed Mater Res*. 1998 Dec. 15; 42(4):491-9; Hollinger, J. O., et al., "Poly(alpha-hydroxy acid) carrier for delivering recombinant human bone morphogenetic protein-2 for bone regeneration," *J. Controlled Rel*., (1996) 39:287–304 and Zegzula, H. D., et al., "Bone formation with use of rhBMP-2 (recombinant human bone morphogenetic protein-2)," *J. Bone Joint Surg*., (1997) 79–A(12): 1778–1790). The bECMs are typically polymeric, biodegradable, and highly porous to mimic the microstructure of bone. Calcium phosphate and polymer/calcium phosphate composite bECMs have also been used (Lu, H. H., et al., "Three-dimensional, bioactive, biodegradable, polymer-bioactive glass composite scaffolds with improved mechanical properties support collagen synthesis and mineralization of human osteoblast-like cells in vitro," *J Biomed Mater Res*. 2003 Mar. 1; 64A(3):465–74; Spitzer, R. S., et al. "Matrix engineering for osteogenic differentiation of rabbit periosteal cells using alpha-tricalcium phosphate particles in a three-dimensional fibrin culture," *J Biomed Mater Res*. 2002 Mar. 15; 59(4):690–6; Marra K G, et al. <<In vitro analysis of biodegradable polymer blend/hydroxyapatite composites for bone tissue engineering," *J Biomed Mater Res*. 1999 Dec. 5; 47(3):324–35). A gene therapy approach to tissue engineering incorporates DNA in the bECM. The DNA transfects local resident cells to secrete desired signaling molecules in a sustained fashion. When the bECM/DNA is implanted into the wound site, the structural matrix serves as an interactive support to wound repair cells that are naturally recruited during the granulation phase of bone wound repair. The cells migrate into the matrix and subsequently come in contact with the incorporated DNA. The ideal matrix would mimic the microstructure of the target tissue, optimize the activity of the expressed growth factors, enhance transfection efficiency of the DNA, provide stability in vivo, and degrade in a controlled fashion with minimal inflammatory response. Additional desirable attributes include controlled release of the gene and ability to promote conducive cell growth and differentiation.

The non-viral gene therapy approach to tissue engineering has been demonstrated by Fang, et al. and Bonadio, et al. (Fang, J., et aL, "Stimulation of new bone formation by direct transfer of osteogenic plasmid genes," *Proc. Natl. Acad. Sci. U.S.A.*, (1996) 93(12):5753–8 and Bonadio, J., et al., "Localized, direct plasmid gene delivery in vivo: prolonged therapy results in reproducible tissue regeneration," *Nat. Med.*, (1999) 5(7):753–9). Fang et al. and Bonadio et al. reported the use of a "Gene Activated Matrix" (GAM) to locally deliver pDNA to wound sites in rats. Fang et al. delivered either a bone morphogenetic protein-4 (BMP-4) plasmid or a plasmid coding for a fragment of parathyroid hormone (amino acids 1–34) (PTH$_{1-34}$). In both cases, a biological response was shown. Both Fang et al. and Bonadio et al. used a collagen-based bECM. However, a major problem with the approach is that they had to use high concentrations of plasmid DNA to achieve a clinical result since collagen based scaffolds do not provide any properties to transfect DNA into the cells. The combination of a biodegradable polymer and plasmid DNA without the addition of a transfecting agent thus appears to yield an inefficient transfection of plasmid DNA into the cell. Hence there is a need for an optimum delivery system that would enhance in vivo gene transfer. To overcome these limitations, researchers are investigating various transfecting agents such as cationic lipids (liposomes or lipoplexes) and/or cationic polymers to incorporate into polymers for tissue engineering applications.

U.S. Pat. Nos. 5,258,044, 5,306,305, 5,543,019, 5,650, 176, 5,676,976, 5,683,461, 5,783,217, 5,843,289, 6,027,742, 6,033,582, 6,117,456, 6,132,463 and 6,214,368 disclose methods of synthesizing calcium phosphate particles and a variety of biomedical uses for nanocrystalline calcium phosphate particles. These patents each describe to varying extents coating of substrates with calcium phosphates, including medical implants and medical devices. The implants and matrices formed from the calcium phosphate materials described in those patents are useful in tissue engineering and repair, especially bone engineering and repair. U.S. Pat. Nos. 5,258,044, 5,306,305, 543,019, 5,650, 176, 5,676,976, 5,683,461, 5,783,217, 5,843,289, 6,027,742, 6,033,582, 6,117,456, 6,132,463 and 6,214,368 are incorporated herein by reference in their entirety for their teachings relating to uses for calcium phosphate.

U.S. Pat. Nos. 5,460,830, 5,441,739, 5,460,831, 5,462, 750, 5,462,751, 5,464,634 and 5,639,505 describe a number of uses for brushite and TCP nanoparticles and various methods for preparing nanocrystalline brushite and TCP by standard methodology using acidic sodium phosphate as a precursors. Calcium phosphate is described in those patents as useful as a bioreactive particle, such as a transfection agent, that is complexed with nucleic acids, proteins and peptides (including antibodies) and pharmacological agents. Also described in those patent references are nanocrystalline calcium phosphate particles coated with viral proteins, useful as viral decoys for immunizing an animal, and nanocrystalline calcium phosphate particles coated with hemoglobin for use as red blood cell surrogates. U.S. Pat. Nos. 5,460,830, 5,441,739, 5,460,831, 5,462,750, 5,462,751, 5,464,634 and 5,639,505 are incorporated herein by reference in their entirety for their teachings relating to uses for calcium phosphate nanoparticles.

Dental Pulp Injury Model to Treat Carious Lesions—For many years, the treatment of dental carious lesions has been based on physical, chemical and biomechanical properties of the restorative materials. In recent years, we have seen the emergence of biological therapies that hold considerable promise to change the practice of dentistry.

The production of dentin under pathological inflammatory conditions often results in poor quality reparative dentin containing irregular deposition of collagen matrix, fewer and wider dentinal tubule and hypomineralization. Clinically, pulpal inflammation with minor exposure is treated with calcium hydroxide (for example Dycal®) using the direct pulp-capping technique. Some of the effects of calcium hydroxide treatment may include reparative dentin formation with preservation of tooth vitality, pulpal resorption, apical lesions and excessive reparative dentin formation. The mechanism of reparative dentin stimulation by Dycal® is that the inherent alkalinity (pH 11–12) of calcium hydroxide induces a focal necrosis upon contact with the pulp and neutralizes the acidity produced during the inflammatory response. This alkalinity may increase the risk of pulp morbidity and apical lesions. The surviving pulp may deposit excessive reparative dentin in response to Dycal®.

Reparative dentin is formed by matrix-mediated biomineralization. The predentin matrix is synthesized and secreted by odontoblasts and is subsequently mineralized to form dentin. After pulp exposure, cytokines are needed to induce cell division to replenish lost cells and transcription factor(s) are required to upregulate the genes encoding the extracellular matrix proteins(ECM). Nakashima has observed that several growth factors induces the proliferation and differentiation of pulp cells (Nakashima, M., "The effects of growth factors on DNA synthesis, proteoglycan synthesis and alkaline phosphatase activity in bovine dental pulp cells," *Arch. Oral Biol.*, (1992) 37(3):231–6 and Nakashima, M., et al., "Regulatory role of transforming growth factor-beta, bone morphogenetic protein-2, and protein-4 on gene expression of extracellular matrix proteins and differentiation of dental pulp cells," *Dev. Biol.*, (1994) 162(1):18–28). Rutherford, et al. have reported that osteogenic protein-1 (OP1 or BMP-7) induces formation of reparative dentin after pulp exposure in monkeys (Rutherford, R. B., et al., "Induction of reparative dentine formation in monkeys by recombinant human osteogenic protein-1," *Arch. Oral Biol.*, (1993) 38(7):571–6).

SUMMARY

A novel method for making hydroxyapatite and the product of that method is provided. The method includes the step of reacting calcium ions with phosphate ions in the presence of hydroxyl ions at a ratio of calcium ions to phosphate ions is greater than 1.67, and typically greater than about 16.7 and even greater than 167. In one embodiment, the phosphate is trisodium phosphate and the calcium is calcium chloride. In that embodiment, the hydroxyapatite is prepared according to the formula:

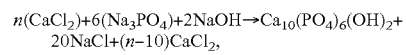

$$n(CaCl_2)+6(Na_3PO_4)+2NaOH \rightarrow Ca_{10}(PO_4)_6(OH)_2+20NaCl+(n-10)CaCl_2,$$

wherein n is greater than 10, and typically greater than 100, or even 1000.

Also provided is a hydroxyapatite complex in which the above-described hydroxyapatite is complexed with a biomaterial. In one embodiment, the biomaterial is plasmid DNA that contains a gene, such as a bone morphogenetic protein gene. Examples of suitable genes include rhBMP-2, Osx, Runx2, PDGF, NGF, VEGF, IGF, FGFs, EGF, TGF-β and BMP-7.

The hydroxyapatite complex can be used to transform cells in vitro or in vivo. A method is therefore provided for transforming cells. The method includes the step of contacting a cell with the described hydroxyapatite complex. The hydroxyapatite may be associated with an appropriate tissue engineering matrix for use in regenerative medicine. A product including the described hydroxyapatite and a substrate, such as a bio-degradable porous natural and/or synthetic polymer, useful in tissue engineering and wound healing also is described.

BRIEF DESCRIPTION OF THE DRAWINGS

FIGS. 3A and 3B show XRD patterns of HAp (3A) with NaOH and (3B) without NaOH at various heating temperatures.

DETAILED DESCRIPTION

Figure 1:
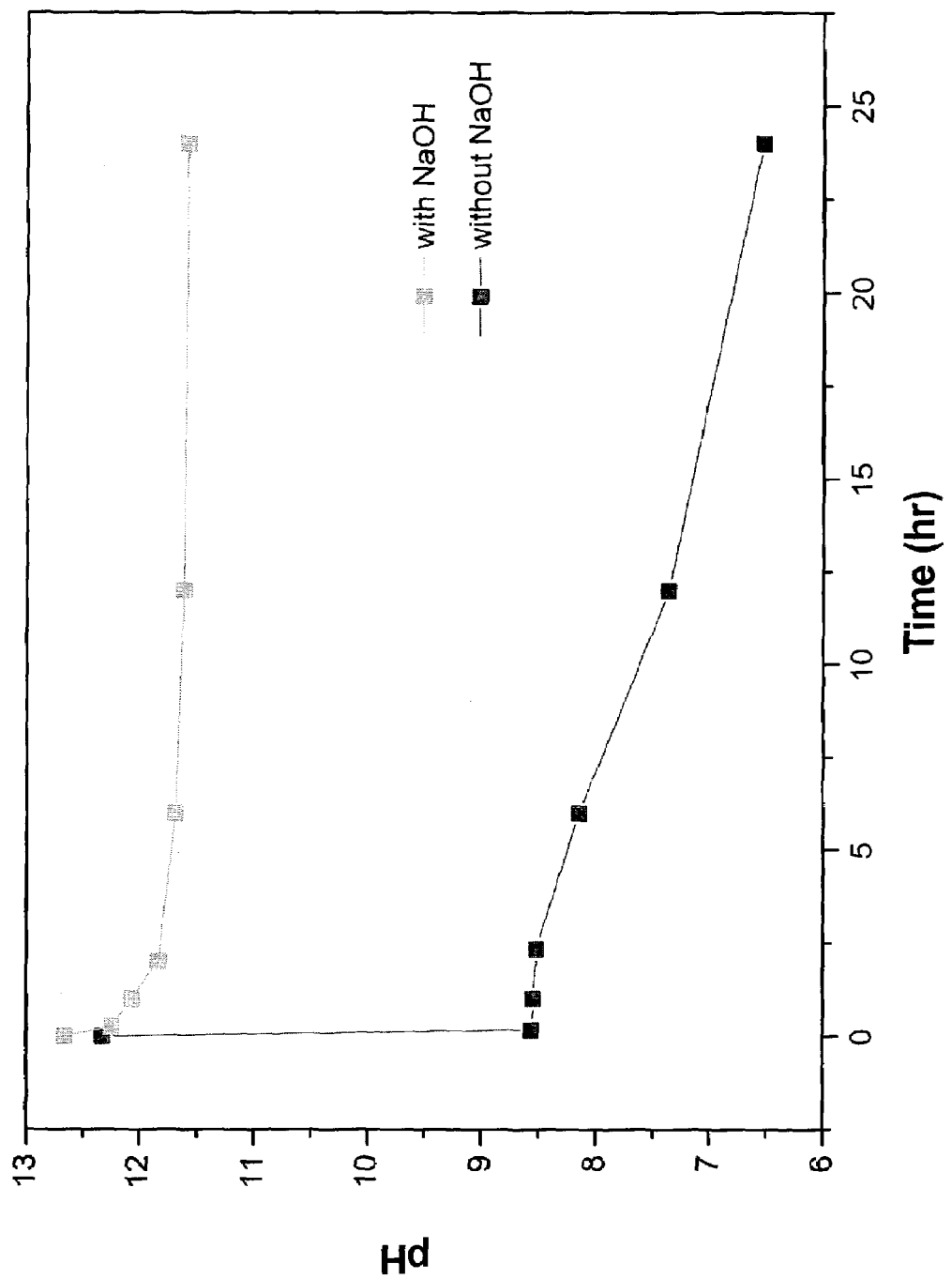
FIG. 1 is a graph showing pH changes over time for hydroxyapatite prepared as described herein.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. Also, the disclosure of these ranges is intended as a continuous range including every value between the minimum and maximum values.

Provided herein is a novel method for the aqueous synthesis of nanocrystalline hydroxyapatite. The method provides superior quality hydroxyapatite and is robust, in that the method does not require stringent pH conditions, as do previous methods for the production of hydroxyapatite. In addition, the approach does not require continuous monitoring of the pH to ensure formation of hydroxyapatite. In the present method, the pH remains invariant during the entire course of the reaction and even beyond over a period of 24 h thus ensuring that the hydroxyapatite formed is entirely stoichiometric with no point defects. It is well known that the current approaches mentioned above (Formulas I and II) undergo significant pH variations and need continuous monitoring of the pH. Furthermore, in the present case, the hydroxyapatite formed is nanocrystalline in nature, superior to commercially-available calcium phosphate transfection reagents in its use as a gene transformation vehicle. The nanocrystalline hydroxyapatite also is useful in tissue engineering as further outlined below.

As used herein, a "gene" is an operative genetic determinant in its broadest sense. A gene includes an "expressed sequence" that encodes a protein or is transcribed into a functional RNA product. A typical gene includes an expressed sequence, along with operably linked regulatory sequences that control expression of the gene, including, but not limited to, promoters, enhancers, operators and terminators. Two sequences are "operably linked" if they are arranged to act in an expected manner in relationship to each other. In a gene, regulatory sequences are operably linked in a manner sufficient to cause correct and/or desired transcription of the expressed sequence in a cell. Promoters can be, for example and without limitation, constitutive or semi-constitutive (for example, CMV and RSV promoters) or tissue-specific promoters (for example, a muscle creatinine kinase (MCK) promoter).

The terms "expression" or "gene expression," and like words and phrases, mean the overall process by which the information encoded in a nucleic acid, typically a gene, is converted into a functional ribonucleic acid, such as a ribozyme, an antisense RNA or an interfering RNA; a protein or a post-translationally modified version thereof; and/or an observable phenotype. Expression of a gene, or the activity of a cellular factor, such as a protein, is "modulated" if the expression or activity of the cellular factor either is up- or down-regulated.

As used herein, a "nucleic acid" may be any polynucleotide or polydeoxynucleotide and, unless otherwise specified includes as a class DNA and RNA and derivatives, conservative derivatives, homologs (a nucleic acid of a different species performing the same function) and analogs thereof. Without limitation, a nucleic acid may be single-stranded or double stranded. A nucleic acid or a protein "analog" is a nucleic acid or peptide containing one or more modified bases and/or a modified backbone.

Nucleic acid analogs may be useful as functional RNA. For example, the RNA analog may be used as antisense RNA, as a ribozyme or as an interfering RNA. Antisense technology is described for instance in U.S. Pat. No. 6,117,273, among a variety of other patents and publications. Interfering RNA technology is described in U.S. Pat. Publication No. 20020173478, Elbashir et al. "Analysis of Gene Function in Somatic Mammalian Cells Using Small Interfering RNAs," *Methods* 26(2) (2002) 199–213, and Xia et al., "siRNA-mediated gene silencing in vitro and in vivo," *Nature Biotechnology*, (October 2002) 20:1006–1010. Xia et al. describes construction of suitable plasmid containing a gene for expression of an siRNA. That reference also describes recombinant viral vectors, in vivo delivery, the appropriate expression of an siRNA hairpin and down-regulation of the expression of the target β-glucuronidase gene in mouse brain and liver, thereby providing proof of concept of the usefulness of siRNA technology in gene transfer.

A "peptide" or "polypeptide" is a chain of amino acids and, unless otherwise specified includes as a class peptides and proteins, post-translationally modified versions of proteins and peptides and derivatives, conservative derivatives, homologs (a protein or peptide from a different species performing the same function) and analogs thereof. A "protein" is a functional, naturally-occurring peptide or a derivative, conservative derivative, homolog or an analog thereof. Proteins and peptides, including fragments, analogs, homologs and derivatives thereof, can be prepared synthetically, i.e., using the well-known techniques of solid phase or solution phase peptide synthesis. Alternatively, polypeptides can be prepared using well known genetic engineering techniques, or affinity purified from biological samples, for example from cells and cell extracts.

A "cell" is understood in its broadest sense to include, without limitation, eukaryotic and prokaryotic cells, including bacteria, fungi, animal and plant cells. A cell is transformed if an exogenous nucleic acid is transferred into the cell and either 1) is transiently or permanently expressed within the cell, or 2) is propagated with the cell.

As noted above, "polypeptides" include those polypeptides having wild-type (wt.) amino acid sequences, but also including the polypeptides modified with conservative amino acid substitutions, as well as biologically active and/or functional fragments, analogs, agonists, homologs and derivatives thereof. The term "biologically active" refers to a specific biological effect of the polypeptide, for example in transforming cells, in promoting tissue growth and correct differentiation in a tissue engineering scaffold, in activation of signal transduction pathways on a molecular level or in induction (or inhibition by antagonists) of physiological effects mediated by the native protein or polypeptide in vivo. A "functional" compound includes "biologically active" compounds, but more broadly means a compound that acts in the manner intended or desired in a biological system or in vitro.

A "biomaterial" includes biologically functional materials and materials of biological origin, including without limitation: nucleic acids; peptides and proteins; polysaccharides; pharmaceutically active compounds or compositions; and binding reagents. Association of a biomaterial, such as plasmid DNA, an interfering RNA or a peptide or protein, with the hydroxyapatite described herein facilitates transfer of that biomaterial into cells and/or action of the biomaterial with respect to the cells. In one embodiment, a biomaterial may be delivered therapeutically by complexing the biomaterial with the hydroxyapatite described herein and delivering the biomaterial by any known and effective manner, including in combination with any useful pharmaceutical delivery vehicle. As used herein, a "hydroxyapatite complex" is hydroxyapatite complexed with, or otherwise associated physically with a second material, such as a biomaterial, drug or chemical compound or composition.

The method for producing hydroxyapatite described herein includes reacting calcium and a non-acidic ionic phosphate, such as trisodium phosphate, in the presence of hydroxyl ions. Previous methods involve reacting acidic phosphates with calcium in a buffered solution to produce calcium phosphates, including hydroxyapatite. The reaction stoichiometry preferably is such that the calcium ions far outnumber the phosphate ions, which prevents the formation of large calcium phosphate crystals. Furthermore, a large number of $Ca^{+2}$ ions will ensure an overall positive charge on the Ca-phosphate-DNA complex. For example, a reaction for the production of hydroxyapatite would proceed according to the following formula:

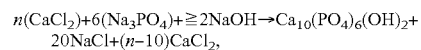

wherein n is greater than 10 and typically from about 50 to about 5000 and most typically from about 100 to about 1000. The relative ratio of $Ca^{+2}$ ions to $PO_4^{-3}$ ions should be sufficiently large to favor production of nanocrystalline hydroxyapatite particles with a diameter in the range of about 1 to about 100 nm. The amount of hydroxide ion should be equal to or in excess of the amount needed to produce stoichiometric amounts of hydroxyapatite, though not in large enough amounts to hamper formation of the nanocrystalline hydroxyapatite.

Although the reaction above uses calcium chloride, trisodium phosphate and sodium hydroxide, suitable substitutes for these compounds are known in the art. Suitable substitutes for calcium chloride include, without limitation, calcium thiocyanate, calcium nitrite, calcium nitrate-hydrate, calcium nitrate-anhydrous, calcium acetate, calcium oxalate, calcium citrate, calcium stearate and a calcium alkoxide (for example, calcium methoxide, ethoxide or propoxide). Suitable substitutes for trisodium phosphate include, without limitation, tripotassium phosphate, tris (tetra-alkyl) ammonium phosphate (alkyl groups can include methyl, ethyl, propyl, butyl etc.) Suitable substitutes for sodium hydroxide include, without limitation potassium hydroxide, ammonium hydroxide, tetraalkyl ammonium hydroxide (alkyl groups include methyl, ethyl, butyl, propyl, etc.). Buffers also may serve as a source of hydroxide ions, including HEPES.

The nanocrystalline hydroxyapatite particles or hydroxyapatite complexes prepared by the methods described herein may be associated with a substrate (incorporated into a substrate or deposited onto a substrate) for a variety of uses, for example and without limitation, in tissue engineering and cell transformation. In one embodiment, the calcium phosphate particles are incorporated into a matrix, such as a biomimetic extracellular matrix, which a synthetic matrix that is intended to mimic a natural extracellular matrix in its structure and/or function. The matrix may be a polymer that is either a natural polymer or a synthetic polymer, or combinations thereof. The polymer typically is a water-swellable polymer, optionally containing water within its matrix. The nanocrystalline hydroxyapatite particles are mixed with the polymer precursors prior to or during polymerization of the polymer or its precursor, or prior to or during cross-linking of the polymers. In one embodiment, the hydroxyapatite particles are added to a solution containing a polymer and the polymer subsequently is cross-linked by standard methods. Including the hydroxyapatite particles in the cross-linking reaction and not in the polymer polymerization reaction ensures complete polymerization of the polymer, while incorporating the hydroxyapatite particles substantially homogenously in the matrix. The hydroxyapatite particles also may be loaded into a pre-formed-swellable polymer matrix. Examples of and methods for post-loading a compound into a hydrogels may be found in PCT Publication Nos. WO 01/91848 and WO 02/02182.

Polymer matrices of use as a tissue engineering substrate as described herein typically are "bioerodible," or "biodegradable," unless a permanent matrix is desirable. The terms "bioerodible," or "biodegradable," as used herein refer to materials which are enzymatically or chemically degraded in vivo into simpler chemical species. Either natural or synthetic polymers can be used to form the matrix, although synthetic biodegradable polymers may be preferred for reproducibility and controlled release kinetics. U.S. Pat. Nos. 6,171,610, 6,309,635 and 6,348,069, which are incorporated herein by reference for their teachings regarding the art of tissue engineering, disclose a variety of matrices for use in tissue engineering. U.S. Pat. No. 6,171,610 discloses use of hydroxyapatite in tissue engineering. The hydroxyapatite prepared by the methods described herein is useful in such an application. In any case, the hydroxyapatite prepared by the methods described herein, for example complexed with a biomaterial such as plasmid DNA, may be associated with any suitable matrix, including without limitation those described herein.

Natural polymers include, but are not limited to, fibrin, collagen, glycosaminoglycans (GAGs), such as chitin, chitosan and hyaluronic acid and polysaccharides, such as starch, ι-, κ- or λ-carrageenan, alginate, heparin, glycogen and cellulose. In one embodiment, as shown for example below, a solution containing fibrinogen and nanocrystalline hydroxyapatite particles which are complexed with a transforming nucleic acid and are then cross-linked by the action of thrombin. Other natural polymers containing the nanocrystalline calcium phosphate particles, or complexes of nanocrystalline calcium phosphate particles with a biomaterial, are prepared in an equivalent manner, by mixing the hydroxyapatite complex with a polymer and then complexing the polymer with a cross-linker, or by any effective manner.

Synthetic polymers include, but are not limited to polylactide (PLA), polylactide-co-glycolide (PLGA), polyglycolic acid (PGA), polyurethanes, polycaprolactone, polymethyl methacrylate (PMMA), polyamino acids, such as poly-L-lysine, polyethyleneimine, poly-anhydrides, polypropylene-fumarate, polycarbonates, polyamides, polyanhydrides, polyortho esters, polyacetals, polycyanoacrylates and degradable polyurethanes. Useful non-erodible polymers include without limitation, polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolifins, polyethylene oxide, polyvinyl alcohol, teflon.RTM., and nylon. Structurally, the polymers may have any useful form, including without limitation, hydrogels, dendrimers, polymeric micellular structures and combinations thereof. Synthetic polymers can be cross-linked or otherwise combined with natural polymers.

For certain tissue engineering applications, attachment of the cells to the polymer is enhanced by coating the polymers with compounds such as basement membrane components, agar, agarose, gelatin, gum arabic, collagens types I, II, III, IV, and V, fibronectin, laminin, glycosaminoglycans, polyvinyl alcohol, mixtures thereof, and other hydrophilic and peptide attachment materials known to those skilled in the art of cell culture. It also may be desirable to create additional structure using devices provided for support, such as struts, or the like. These can be biodegradable or non-degradable polymers, which are inserted to form a more defined shape than is obtained using the cell-matrices.

The use of a fibrin matrix might be preferred in many instances over other natural or synthetic matrices, for example when the matrix is used for wound healing purposes, such as in bone wound-healing. The nanocrystalline calcium phosphate particles carriers' role is to enhance DNA transfection into mammalian cells. In order to achieve this goal in a bone wound, for instance as shown in Example 4, below, the calcium phosphate particles are incorporated into a matrix serving as an interactive support to the wound repair cells that are naturally recruited during the granulation phase of bone wound repair. The cells migrate into the matrix and subsequently come in contact with the calcium phosphate/pDNA particles resulting in incorporation of the DNA. The ideal gene delivery matrix would enhance transfection efficiency of the DNA, provide stability in vivo, and degrade in a controlled fashion with minimal inflammatory response. Additional desirable attributes include controlled release of the gene and ability to be conducive to cell growth and differentiation. A bone fracture, in general, will heal spontaneously, restoring form and function if the distance or size of the defect is small. Spontaneous bone formation will not occur when the bone defect exceeds a certain size, referred to as the critical-sized defect (CSD). The compositions and methods described herein could be used in repair of a critical size defect to restore form and function of the bone (Bolander, M. E., "Regulation of fracture repair by growth factors," *Proc. Soc. Exp. Biol. Med.* 1992; 200: 165–170; Reddi, A. H., "Initiation of fracture repair by bone morphogenetic proteins." *Clin. Orthop. Rel. Res.* 1998; 355S: S66–S72; Barnes, G, et al., "Growth factor regulation of fracture repair," *J. Bone Min. Res.* 1999; 14(11):1805–1815 and Hollinger, J. O., et al., "Poly(alpha-hydroxy acids): Carriers for bone morphogenetic proteins," *Biomaterials* 1996; 17(2): 187–194).

The nanocrystalline calcium phosphate particles are versatile and could be injected directly into a wound with pDNA bound and packaged to them, or they could be incorporated in one or more matrices. The choice of an optimal matrix would vary depending on the wound type. As described herein, the matrices could be of natural origin, such as fibrin, or synthetic polymers such as PLA, PGA and PLGA, and a variety of hydrogels that are thermo-sensitive, photo-sensitive, pH-sensitive, electrical field sensitive or magnetic field sensitive. Fibrin may be preferable in many instances for various reasons. For example fibrin provides a foundational substratum for wound healing elements and angiogenesis. Fibrin is an integral wound repair component supporting cell anchorage, signaling molecule sequestration and localization, and cell differentiation.

A tissue-engineered plasmid DNA delivery system preferably is biodegradable and biocompatible at implantation. It must localize, protect the pDNA, promote cell attachment and ingress, support osteoconduction and angiogenesis, and erode concurrently with bone formation. These stringent requirements can be fulfilled by fibrin designs (Hollinger, J. O., et al., Role of bone substitutes, *Clin. Orthop.*, (1996) (324):55–65; Hollinger, J. O. and K. Leong, Poly(alpha-hydroxy acids): carriers for bone morphogenetic proteins, *Biomaterials*, (1996) 17(2):187–94; Hu, Y., Hollinger, J. O., and Marra, K. G., Controlled release from coated polymer microparticles embedded in tissue-engineered scaffolds, *J. Drug Target.*, (2001) 9(6):431–8; Lasa, C., Jr., et al., "Delivery of demineralized bone powder by fibrin sealant," *Plast. Reconstr. Surg.*, (1995) 96(6):1409–17; discussion 1418 and Amrani, D. L., et al., Diorio, and Y. Delmotte, "Wound healing. Role of commercial fibrin sealants," *Ann. N. Y. Acad. Sci.*, (2001) 936:566–79). The degradation rate and porosity for fibrin can be controlled (Nowotny, R., et al, "Preparation of fibrin clot samples for tensile stress-strain experiments," *Biomaterials*, (1981) 2(1):55–6 and Carr, M. E., Jr., et al., "Effect of fibrin structure on plasmin-mediated dissolution of plasma clots," *Blood Coagul. Fibrinolysis*, (1995) 6(6):567–73.) Furthermore, fibrin-bound nanocrystalline calcium phosphate particles/pDNA is more resistant to enzymatic degradation than naked DNA. Resistance to enzymatic degradation will improve DNA uptake and survival for osteogenesis.

In addition to the hydroxyapatite and hydroxyapatite complexes described herein, it may be desirable to add one or more additional biomaterials to a cell growth matrix or medium. These additional biomaterials may or may not be complexed with the hydroxyapatite described herein. These biomaterials include growth factors, angiogenic factors, compounds selectively inhibiting ingrowth of fibroblast tissue such as anti-inflammatories, and compounds selectively inhibiting growth and proliferation of transformed (cancerous) cells. These biomaterials may be utilized to control the growth and function of implanted cells, the ingrowth of blood vessels into the forming tissue, and/or the deposition and organization of fibrous tissue around the implant. Examples of growth factors include heparin binding growth factor (hbgf), transforming growth factor alpha or beta (TGFα or TGFβ), alpha fibroblastic growth factor (FGF), epidermal growth factor (EGF), vascular endothelium growth factor (VEGF), some of which also are angiogenic factors. Additional factors include hormones, such as insulin, glucagon, and estrogen. In some embodiments it may be desirable to incorporate factors such as nerve growth factor (NGF) or muscle morphogenic factor (MMP). Steroidal antiinflammatories can be used to decrease inflammation to the implanted matrix, thereby decreasing the amount of fibroblast tissue growing into the matrix. These biomaterials are known to those skilled in the art and are available commercially or are described in the literature. The biomaterials may be incorporated to between one and 30% wt. (percentage by weight), although the biomaterials may be incorporated to a broader range of weight percentage between 0.01% wt. and 95% wt, or even beyond that range depending on the specific activity (activity per unit weight or volume) of the biomaterial.

Biomaterials can be incorporated into the matrix and released over time by diffusion and/or degradation/erosion of the matrix, they can be suspended with the cell suspension, they can be incorporated into microspheres which are suspended and distributed among the cells or associated with the matrix, or some combination thereof. Microspheres typically would be formed of materials similar to those forming the matrix, selected for their release properties rather than structural properties. Release properties also can be determined by the size and physical characteristics of the microspheres.

Medical devices can be coated with the hydroxyapatite and hydroxyapatite complexes prepared according to the methods described herein. Medical devices include medical implants as are known in the art, such as bone implants and stents. A variety of methods are known in the art for deposition of hydroxyapatite onto such devices. In one example, the devices are coated with a hydroxyapatite-containing or hydroxyapatite complex-containing polymer film prepared as described herein and coated onto an implant, for example, as described in U.S. Pat. No. 5,306,305. This method would be particularly suited to uses that require association of a bioactive material onto the implant. Other uses for the hydroxyapatite described herein require only pure hydroxyapatite, and do not require that a complexed biomaterial survive the deposition process. In such a case, the electrodeposition methods described, for example and without limitation, in U.S. Pat. Nos. 5,258,044 and 5,543,019 may be used to deposit the hydroxyapatite onto the device.

The hydroxyapatite described herein is a material useful for any purpose to which hydroxyapatite is suited, whether or not related to its use in bio-engineering or biotechnology applications. The hydroxyapatite described herein, however, finds use in the biomedical field in a bone or tooth matrix and for its cell transformation capabilities. The hydroxyapatite described herein is useful in tissue engineering as described above, in the United States patents described above and as is shown in the Examples below. The hydroxyapatite or hydroxyapatite complexes may be associated with a biodegradable or bioerodable matrix, for instance it can be incorporated into a matrix as described above or may be deposited onto or imbibed into such a matrix. Cells can be grown on or within in the matrix, either in vitro or in vivo.

One particularly surprising result, as shown in the examples below, is that when the hydroxyapatite described herein is complexed with DNA it forms a particularly potent cell transfection material. Calcium phosphate materials, including hydroxyapatite, have a long history of use as a cell transformation vehicle. Watson et al. RECOMBINANT DNA, Second Edition, Scientific American Books, 1992, p. 215. As shown below, the hydroxyapatite described herein, when complexed with a transforming nucleic acid (a nucleic acid capable of transforming a cell), can transform cells with surprising efficiency, with a multi-fold increase as compared to commercially-available calcium phosphate transformation systems, even at conditions optimized for the commercial systems. In use, the nucleic acid is complexed with the hydroxyapatite by including the nucleic acid either in the phosphate-containing solution or the calcium-containing solution prior to mixing of the two solutions to form the hydroxyapatite. The hydroxyapatite complex is prepared by mixing the two solutions. Cells to be transformed with the nucleic acid then are contacted with the hydroxyapatite complex for a time sufficient to produce a desired degree of transformation. This is determined empirically, by a time-course study correlating transformation efficiency with the time of transformation. In vitro experiments with cell lines are described in the Examples below. Transformation of cells in vitro is nevertheless only one use for the transformative capacity of the nanocrystalline hydroxyapatite-nucleic acid complexes described herein.

As shown herein, nanocrystalline hydroxyapatite complexed with nucleic acid may be incorporated into a hydrogel matrix, particularly a biodegradable or bioerodable matrix to transform cells in vivo. As shown in the data below, nanocrystalline hydroxyapatite complexed with DNA containing a gene encoding rhBMP-2 was incorporated into a fibrin matrix, which was then implanted into muscle. Over time, the matrix became electron-dense, indicating successful transformation with the rhBMP-2 gene. Other genes are predictably useful in a similar manner, such as, without limitation, members of the bone morphogenetic protein (BMP) subgroup of the transforming growth factor beta supergene family. Specific examples of potentially useful genes include, without limitation rhBMP-2, BMP-4, Osx, Runx2, NGF, EGF, PDGF, IGF, TGF-β, VEGF and BMP-7. A biologically active nucleic acid, such as a nucleic acid containing any suitable gene, is complexed with nanocrystalline calcium phosphate and incorporated into a matrix. The matrix is then deposited/inserted into a suitable site in vivo. The matrix can be seeded with suitable progenitor cells or optionally deposited without cells, with the object that endogenous cells migrate into the matrix. The site of insertion either is the site in a permanent recipient where the engineered tissue will be permanently located, such as in a tooth or bone, or at a site where the engineered tissue is grown, to be transplanted at a later time to the ultimate recipient. In the second instance, one such site that commonly is used for tissue engineering purposes is the omentum. In that instance, a matrix, optionally seeded with suitable progenitor cells, is implanted into the omentum. Once the engineered tissue prepared and is matured into a suitable differentiated organ or other structure, it is transplanted into a suitable host. Typically the organ or other structure is grown in an immunocompromised host and the organ later is transferred into a suitable permanent recipient. Though use of a matrix may be preferred in some instances for tissue engineering purposes, the hydroxyapatite complex may be deposited into a suitable site in vivo without a matrix, for example as a solution, gel or solid, to elicit a desired biological effect. For example, the hydroxyapatite complex may be injected intravenously, intramuscularly, intraperitoneally, or by any desirable route. Additionally, tissue such as skin or a wound may be washed with a suitable solution containing the hydroxyapatite complex.

Depending on the ultimate use for the hydroxyapatite complex described herein, the complex can be formulated in a variety of appropriate and effective forms. For example, for topical application of a hydroxyapatite complex to the skin, the complex may be formulated into a pharmaceutically-acceptable ointment, salve, balm or lotion as are known in the art. For oral ingestion, the complex may be formulated into a capsule, tablet, liquid or other suitable dosage form as are known in the art. Other dosage forms, such as intravenous, otic, ocular, suppository, transmucosal, subcutaneous or transdermal dosage forms can be prepared in any manner known in the art. For all dosage forms, the hydroxyapatite can be formulated with any suitable excipient (vehicle) as is known, including without limitation, diluents, lubricants, coatings, capsules, emulsifiers, adjuvants, buffers, solvents, matrices, colorants, flavorings, sweeteners, humectants and thickening agents.

The hydroxyapatite complex may be delivered as an immune-modulating composition, for example as a vaccine. The immune-modulating composition also may be injected or otherwise introduced into a host animal to elicit a desired immune response, for example as part of a process to produce polyclonal or monoclonal antibodies. When used in an immune-modulating composition, the hydroxyapatite can be formulated with a suitable adjuvant.

The hydroxyapatite may be used as a gene delivery vehicle as described in brief above. In its simplest form, the hydroxyapatite-DNA complex can be used alone in an aqueous solution, for instance suspended in normal saline. The complex may be associated with a synthetic or natural polymer either to enhance viscosity or to produce a gel or a formed matrix. The synthetic or natural polymers used may be in different forms, including: spheres (hollow or solid), rods (hollow or solid), tubes, fibrils, sheets, foams and otherwise porous polymer structures, wovens, nonwovens, tablets, capsules, meshes, membranes, plugs, stents, plates, sutures, films and sprays (including aerosol sprays incorporated into suitable inhaler devices). The synthetic or natural polymers could be degradable or non-degradable, porous or non-porous.

The hydroxyapatite complexes may be used in many clinical and basic science applications, including: gene replacement therapy, as a pharmacological agent to treat diabetes, osteoporosis, and a host of other diseases, to engineer stem cells to introduce specific growth factor genes and any other genes to influence the differentiation pathway, for drug delivery in all organs of the body, for bone tissue engineering; for cartilage tissue engineering. Other tissue that the hydroxyapatite complexes could be used for in a therapeutic capacity include: liver, kidney, lungs, stomach, brain, muscle spine, ligament, tooth, periodontal structures. pancreas, eyes and nerve. In one use, a paste can be formulated with the hydroxyapatite complex to facilitate wound healing.

Specific therapeutic examples include: direct injection of the complexes into the heart to deliver the gene VGEF to induce angiogenesis for the treatment of ischemic limbs; direct injection of the complexes into the muscle to deliver genes to eliminate scar tissue formation. This has great application in sports medicine, and direct injection of the complex into knee ligaments for ligament repair.

In dental applications, the complexes might be incorporated on material surfaces such as dental implants to deliver an osteogenic gene to enhance implant osteointegration, pulp gene delivery, to treat caries and induce dentin formation. In such an application, the hydroxyapatite complex is incorporated in a polymer natural or synthetic (resorbable or not resorbable) that could be used in periodontal defects (single rooted teeth, multi rooted teeth and furcation involvement and extraction sockets), and incorporated in a synthetic or natural polymer for use in oral surgery and cleft palate.

In the dental applications, a variety of structures can be used to repair the damaged tooth. In one embodiment, the hydroxyapatite complex containing DNA for expressing a suitable regenerative gene is incorporated into a polymer matrix and implanted in a damaged portion of a tooth. Periodontal membrane may be overlayed or the matrix may be occluded by other methods, such as be sealing with a polymer.

In one embodiment, the polymer/hydroxyapatite complex may be multi-layered to create a multi-layered structure. In one example, to treat periodontal disease, a first (tooth side) layer contains a first gene, such as an amelogenin gene, complexed with hydroxyapatite, the second layer contains a second gene, such as BMP-3, complexed with hydroxyapatite and the third layer (defect side) contains a third gene, such as BMP-2, complexed with hydroxyapatite. In another example for periodontal treatment, the hydroxyapatite-complexed DNA will be injected in a hydrogel or other synthetic and/or natural polymers in a periodontal defect.

EXAMPLE 1

Hydroxyapatite was chemically synthesized using $CaCl_2$ and $Na_3PO_4$ in water. The overall chemical reaction in aqueous route can be described as follows:

$$10CaCl_2 + 6Na_3PO_4 + 2NaOH \rightarrow Ca_{10}(PO_4)_6(OH)_2 + 20NaCl$$

In the reaction, 1.3293 g $Na_3PO_4$ was added to 80 mL water and the $Na_3PO_4$ was dissolved by mixing for 30 minutes. To the $Na_3PO_4$ solution was added 0.1080 g NaOH, which was stirred for 30 additional minutes. To form nanocrystalline hydroxyapatite, 1.5 g of $CaCl_2$ (100 mL of 0.135 M $CaCl_2$) was added to the $Na_3PO_4$/NaOH solution and the solution was mixed for 24 hours. After the reaction, the by-product NaCl was removed by periodic washing with water followed by centrifuging the solution. The resultant paste obtained was dried in air.

The hydroxyapatite powders obtained after drying were heated to 1000° C. in air to analyze its thermal stability. The chemical composition and stoichiometry of the synthesized hydroxyapatite was analyzed by investigating its thermal stability in the presence and absence of NaOH. The morphology of the as-prepared and heat-treated powders was observed under the SEM after coating the powders with carbon.

Results

The pH of the reaction shows an abrupt initial drop and a gradual decrease in pH for the synthesis of Hydroxyapatite without the addition of NaOH. However, the formation of Hydroxyapatite with NaOH addition does not show a rapid drop in pH. Barring a slight initial drop, the pH appears to be stable ≈11.5. Most of the reaction for Hydroxyapatite prepared with NaOH is completed within a few hours of the reaction. The as-prepared Hydroxyapatite synthesized under these two conditions exhibit almost identical XRD and FT-IR spectra. However, after heating to high temperature (900° C.), completely different results are obtained for the two cases.

Hydroxyapatite obtained with the addition of NaOH was stable up to 1000° C. in air, but Hydroxyapatite obtained without NaOH transformed to TCP (tricalcium phosphate) when heated above 600° C. This phase transformation of Hydroxyapatite to TCP is indicative of the calcium deficiency (Ca/P<1.67) in the synthesized Hydroxyapatite.

Based on the XRD and FT-IR results, the possible reaction pathways for the formation of Hydroxyapatite in the two cases can be proposed as follows:

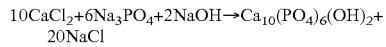

$$10CaCl_2+6Na_3PO_4+2NaOH \rightarrow Ca_{10}(PO_4)_6(OH)_2+20NaCl$$

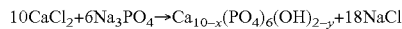

$$10CaCl_2+6Na_3PO_4 \rightarrow Ca_{10-x}(PO_4)_6(OH)_{2-y}+18NaCl$$

The pH—of the solution was measured using pH meter (Accumet 916, Fisher Scientific) and electrode (AccuTupH+, Fisher Scientific). The pH change corresponding to four batches of experiments was observed for a period of 24 h. The initial pH of both solutions were above 12 which is possibly due to the following reaction:

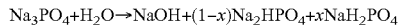

$$Na_3PO_4+H_2O \rightarrow NaOH+(1-x)Na_2HPO_4+xNaH_2PO_4$$

When $CaCl_2$ is dissolved in water, it could undergo hydrolysis yielding an acidic solution due to the following reaction:

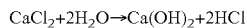

$$CaCl_2+2H_2O \rightarrow Ca(OH)_2+2HCl$$

The reaction of $Na_3PO_4$ and $CaCl_2$ is quite rapid since one solution creates a basic condition and the other an acidic environment yielding a rapid drop in the pH immediately following the reaction.

As shown in FIG. 1, the pH of the Hydroxyapatite synthesized with the addition of NaOH however shows a slight decrease in pH after mixing the two reactants indicating the occurrence of the reaction. There is also no further change in pH indicating that the reaction is almost complete. However, Hydroxyapatite synthesized without NaOH shows considerable changes in pH even after 2 h indicative of the multistep reaction.

Figure 2:
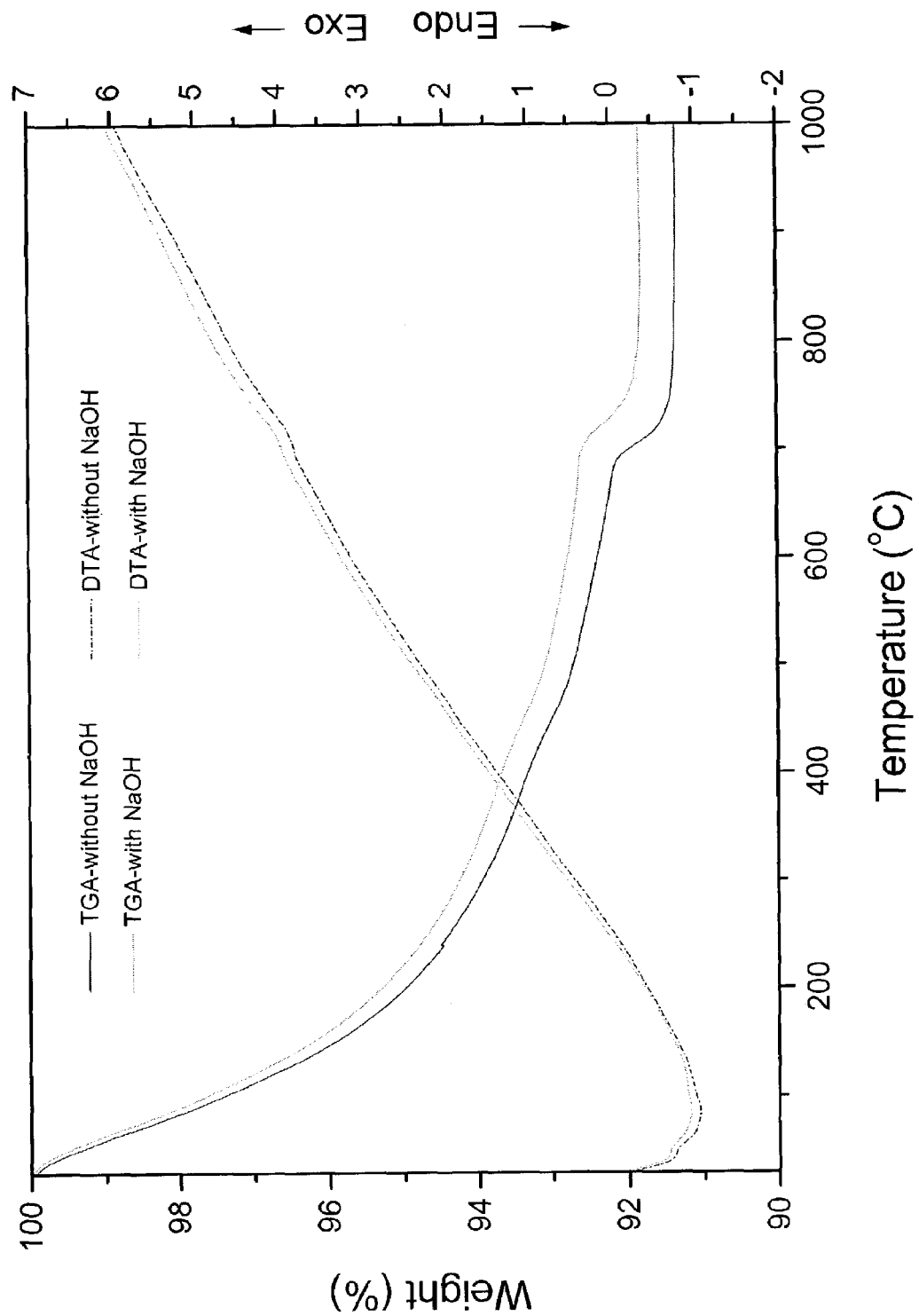
FIG. 2 shows DTA/TGA graphs of HAp with and without NaOH addition.

DTA/TGA—Both differential thermal (DTA) and differential thermogravimetric (DTGA) analyses were conducted using TA Instrument (SDT 2960). The analyses were performed in air employing a heating rate of 5° C./min from room temperature to 1000° C. Results are shown in FIG. 2. The weight loss up to 450° C. is due to the removal of absorbed, adsorbed and lattice water. The weight loss for Hydroxyapatite prepared without NaOH was greater than the case with NaOH. The carbonate introduced into hydroxyapatite during synthesis in the aqueous environment when phosphate groups are substituted with carbonate at high pH when the reaction is conducted in air are removed in the 400–950° C. temperature range.

The abrupt drop in weight for Hydroxyapatite obtained in both processes around 700° C. might be due to the dehydration of Hydroxyapatite forming oxyhydroxyapatite (OHAp). However, a more detailed study is needed to validate this. The calcium deficient Hydroxyapatite decompose into β-TCP and CaO accompanied by slight weight loss which is difficult to detect via TGA. The decomposition reaction is as follows:

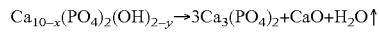

$$Ca_{10-x}(PO_4)_2(OH)_{2-y} \rightarrow 3Ca_3(PO_4)_2+CaO+H_2O\uparrow$$

XRD—The phase purity of the synthesized and heat-treated powders was analyzed by x-ray diffraction using Rigaku diffractometer operating at 35 kV and a current of 20 mA (CuKα) at a 2θ range of 10 to 80° employing a step size of 0.05 and a 2 second exposure. Results are shown in FIGS. 3A and 3B. The hydroxyapatite has the strongest XRD peak at 31.7° with crystallographic space group notation of $P6_3/m$. On the other hand, β-TCP (whitlockite) has the strongest XRD peak at 31.1° with the space group notation R-3c. β-TCP is formed when Hydroxyapatite synthesized without the addition of NaOH was heated up to 900° C. The Hydroxyapatite to β-TCP transition is a strong indication of calcium deficient Hydroxyapatite. The broad XRD peaks for the as-prepared Hydroxyapatite gets sharper as the heat treatment temperature increases due to grain growth, coarsening of the crystallites.

Figure 4A:
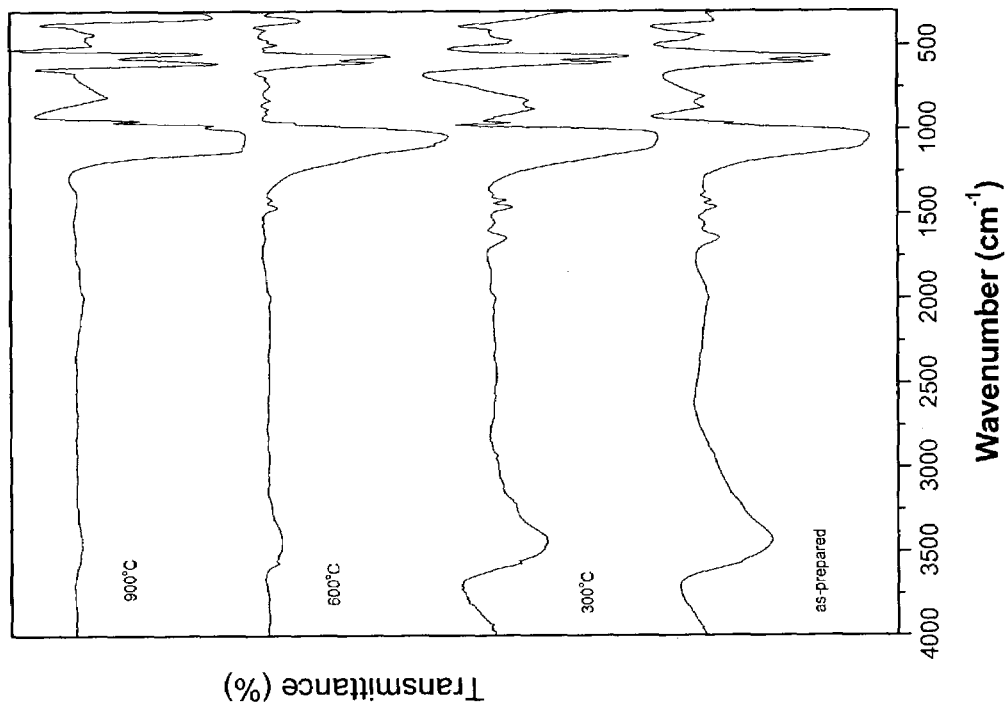
FIGS. 4A and 4B show FT-IR spectra of HAp (4A) with NaOH and (4B) without NaOH at various heating temperatures.
Figure 4B:
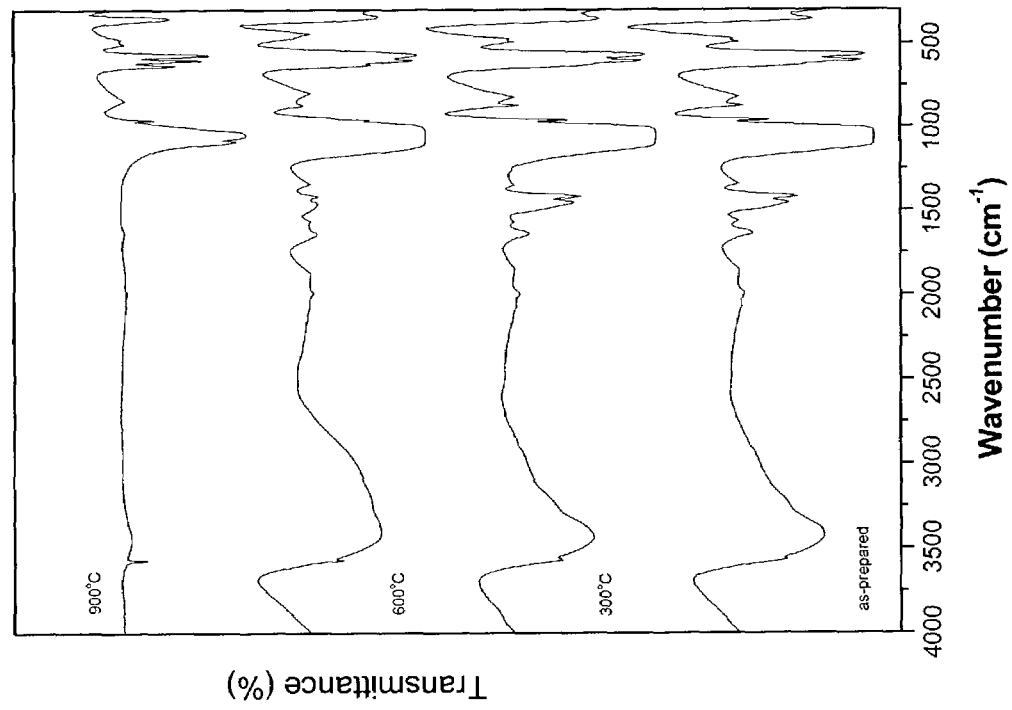

FT-IR—The FT-IR spectra were collected using a Mattson Galaxy Series FT-IR 5000 in the range 4000 to 300 $cm^{-1}$. One milligram of the sample was mixed with 200 mg of KBr powder and pressed into a pellet by applying a 1000 psi pressure (Carver press). Results are shown in FIGS. 4A and 4B. Characteristic FT-IR absorption peaks of Hydroxyapatite are provided in Table 1.

TABLE 1

| (prior art)[1,2] | |
|---|---|
| Absorption | Wavenumber |
| H—O stretching | 3567 $cm^{-1}$ |
| H—O bending | 633 $cm^{-1}$ |
| Absorbed water | 3440 $cm^{-1}$ |
| Carbonate | |
| $\nu_3$ | 1452 $cm^{-1}$ |
| $\nu_2$ | 863 $cm^{-1}$ |
| $PO_4\ \nu_1$ | 960 $cm^{-1}$ |
| $PO_4\ \nu_4$ | 603 $cm^{-1}$ |
|  | 563 $cm^{-1}$ |
| Carbonyl stretching | 1780–1680 $cm^{-1}$ |

[1] M. Toriyama, Y. Kawamoto, T. Suzuki, Y. Yokogawa, K. Nishizawa and H. Nagae, Journal of the Ceramic Society of Japan. Int. Edition, 1992, 100, p939–943.
[2] Toshiyuki Ikoma and Atsushi Yamazaki, Journal of Solid State Chemistry, 1999, 144, p272–276.

The H—O stretching band at 3567 cm$^{-1}$ confirms the formation of Hydroxyapatite along with the strongest XRD peak at 31.7°. The Hydroxyapatite synthesized without NaOH shows no H—O stretching peak at 900° C. This confirms the transformation of Hydroxyapatite to β-TCP phase consistent with the XRD data. The carbonate peak is due to the substitution of phosphate groups by carbonate at high pH when the reaction is conducted in air. This carbonate absorption decreases with increase in temperature in the 400–950° C. temperature range. Carbonate substitution, however, does not diminish the biocompatible characteristics of Hydroxyapatite. The stronger absorption peak of carbonate group at 1452 cm$^{-1}$ and 863 cm$^{-1}$ can be observed for Hydroxyapatite synthesized with NaOH addition.

Figure 5:
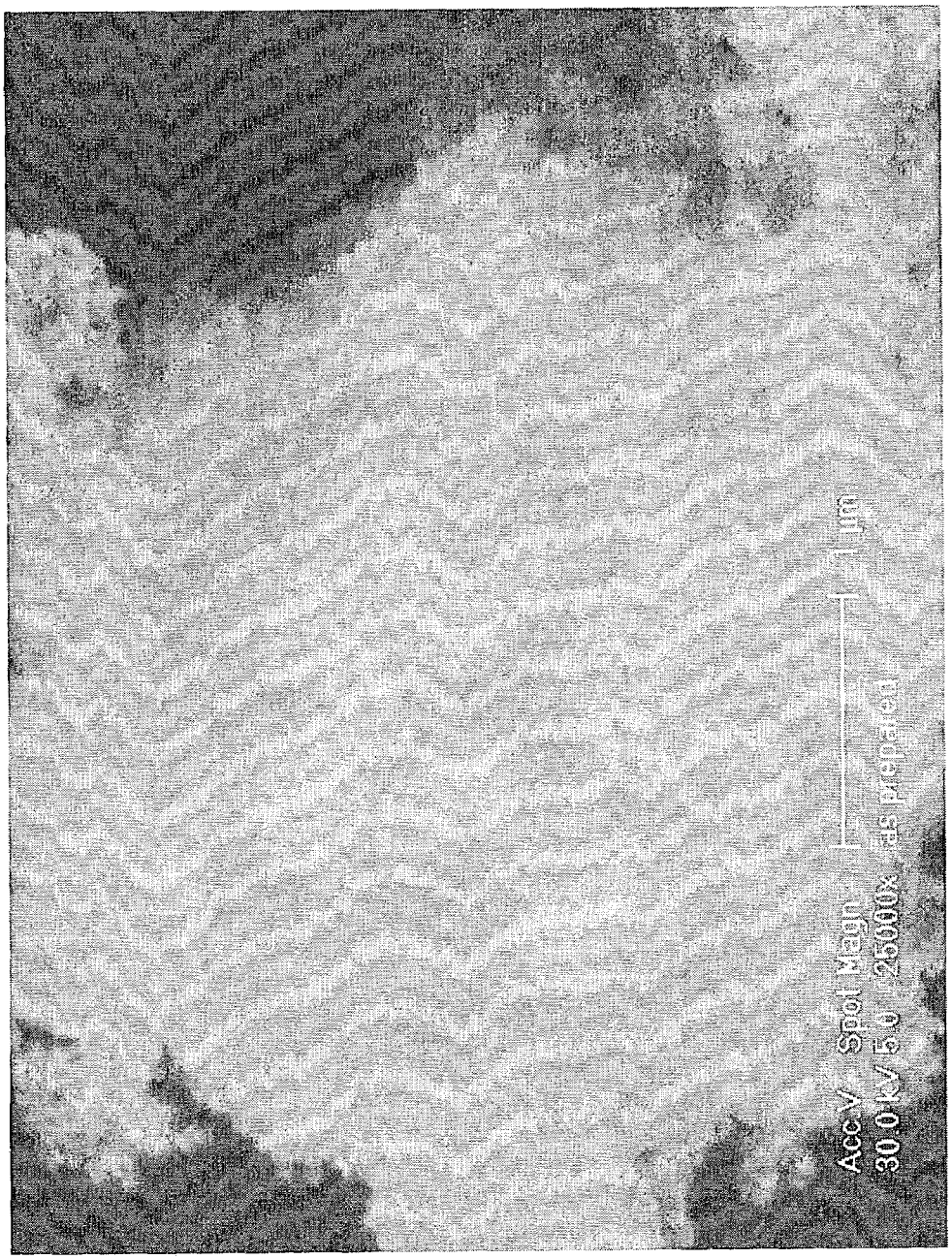
FIG. 5 is a scanning electron microscope (SEM) micrograph of the as-prepared HAp obtained with addition of NaOH showing nano-crystalline (<100 nm) agglomerates (>>2~5 mm).
Figure 6:
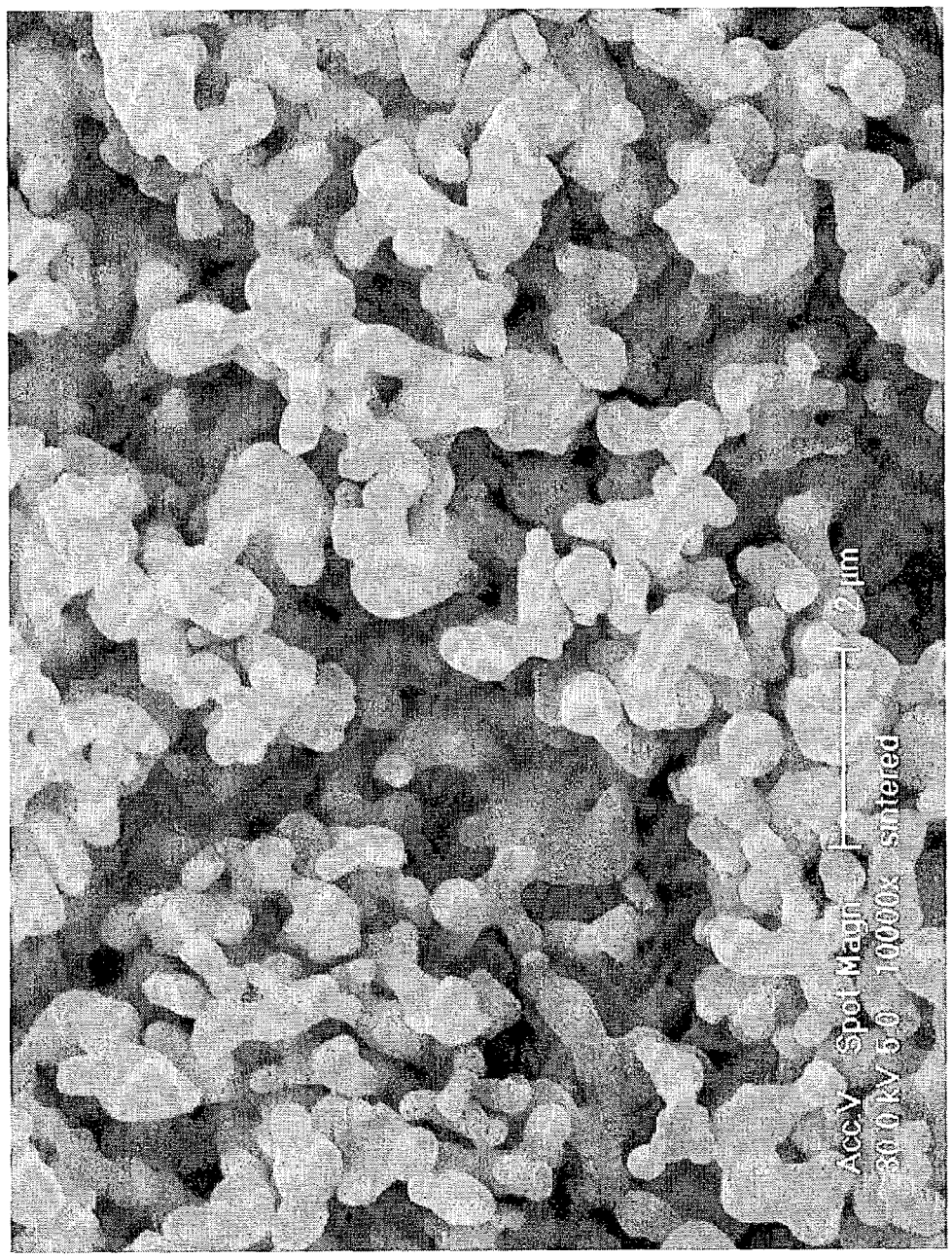
FIG. 6 is a SEM micrograph of stoichiometric HAp heat treated to 900° C. for 10 h in air.

SEM—The powders were coated with carbon using a Polaron 6100 Sputter Coater System. The images were taken using Phillips XL 30 FEG SEM. All the images were collected using the secondary electron mode. Images are provided in FIGS. 5 and 6. The microstructure of the as-prepared Hydroxyapatite powder shows nano-sized (<100 nm) Hydroxyapatite crystallites aggregated into agglomerates (≈2~5 μm). The Hydroxyapatite powder heat-treated at 900° C. for 10 h in air shows a uniform distribution of larger crystallites (<1 μm). This increase in crystallite size can be also confirmed by the peak broadening analysis of the XRD data using the Scherrer equation.

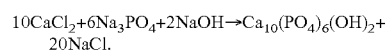

$$T = 0.9\lambda/B \cos \theta_B \quad B = \theta_1 - \theta_2$$

where, T: thickness of the crystallites λ: wavelength (CuKα=1.5406 Å)

The broad XRD peaks for the as-prepared Hydroxyapatite is sharpened as the heat treatment temperature is increased due to coarsening of the crystallites.

In conclusion, the Hydroxyapatite powder obtained at high pH using NaOH was stable at high temperatures. Hydroxyapatite synthesized at low pH without the addition of NaOH transformed into β-TCP, characteristic of other calcium deficient Hydroxyapatite synthesized by using various low temperature chemical methods.

The presence of Hydroxyapatite and the formation of β-TCP was confirmed using both XRD and FT-IR analysis. The as-prepared Hydroxyapatite shows agglomerates of nano-crystalline Hydroxyapatite (<100 nm). However, heat-treated Hydroxyapatite shows uniform <2 μm sized crystals.

EXAMPLE 2

Plasmid Gene Delivery Using Nanosized Calcium Phosphate Particles

Figure 7:
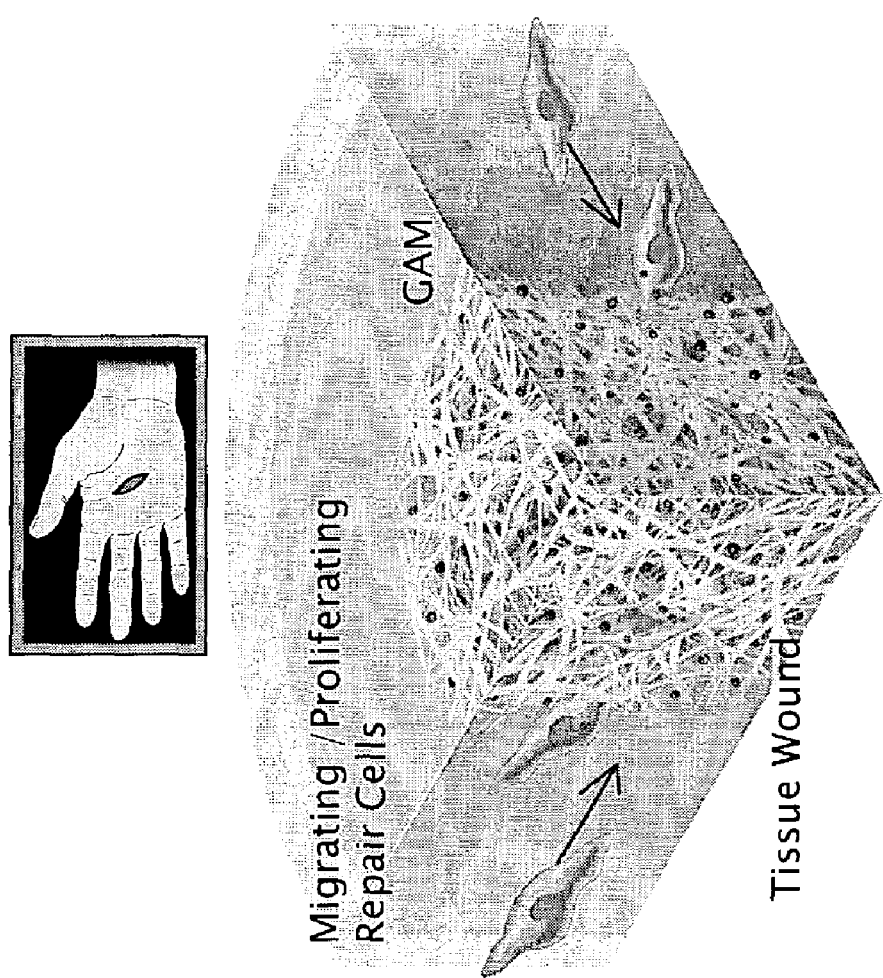
FIG. 7 (prior art) is a schematic drawing showing wound healing. Bonadio. *J. Mol Med.* (2000) 78:303–311.

As shown schematically in FIG. 7, one use for gene delivery is in tissue engineering or reconstruction. In these methods, a gene activated matrix (GAM) is provided in which DNA is incorporated into a structural matrix. When the GAM is inserted at a desired location in vivo, for example in bone tissue as a bone growth matrix, granulation tissue fibroblasts proliferate and migrate from viable tissue surrounding the bone wound. The cells then uptake and transiently express plasmid DNA and will act as local in vivo bioreactors, producing plasmid-encoded proteins that stimulate bone healing (Boniado (2000), *J. Mol. Med.* 78:303–311).

It is therefore desired to develop a non-viral gene delivery carrier, such as, without limitation, a GAM, that provides improved transfection efficiencies through the addition of a transfecting agent such as calcium phosphate (calcium phosphate).

The delivery system described herein comprises two components. The first component are calcium phosphate (hydroxyapatite) nanocarriers. The second component is the plasmid DNA (pDNA) bound to the hydroxyapatite nanocarriers, used for efficient transfection.

Hydroxyapatite nanocarriers have several advantages over other calcium phosphate transfection techniques including controlled loading of pDNA and enhanced pDNA transfection into the cell.

Synthesis of Nanocrystalline Hydroxyapatite for Gene Delivery

Hydroxyapatite was chemically synthesized using $CaCl_2$ and $Na_3PO_4$ in deionized water. The overall chemical reaction in aqueous route can be described as follows:

$$10CaCl_2 + 6Na_3PO_4 + 2NaOH \rightarrow Ca_{10}(PO_4)_6(OH)_2 + 20NaCl.$$

Figure 8A:
FIG. 8A is a SEM micrograph showing the morphology of the nanocrystalline hydroxyapatite particles described herein.
Figure 8C:
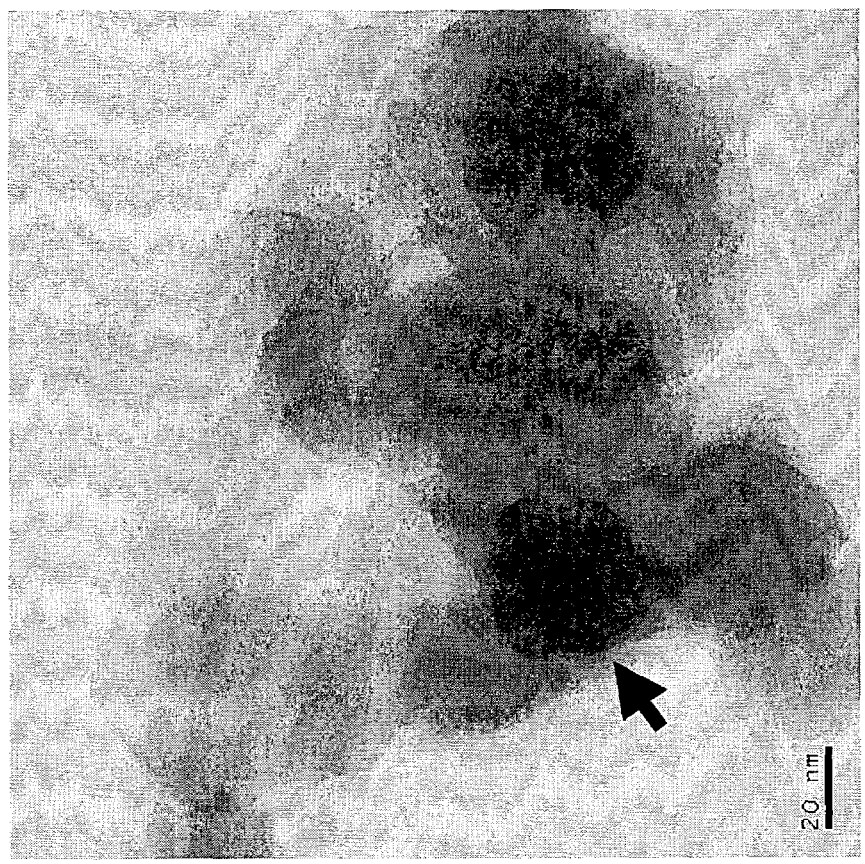
FIGS. 8B and 8C are Transmission Electron Microscopy micrographs showing the morphology of the nanocrystalline hydroxyapatite particles described herein.
Figure 8B:
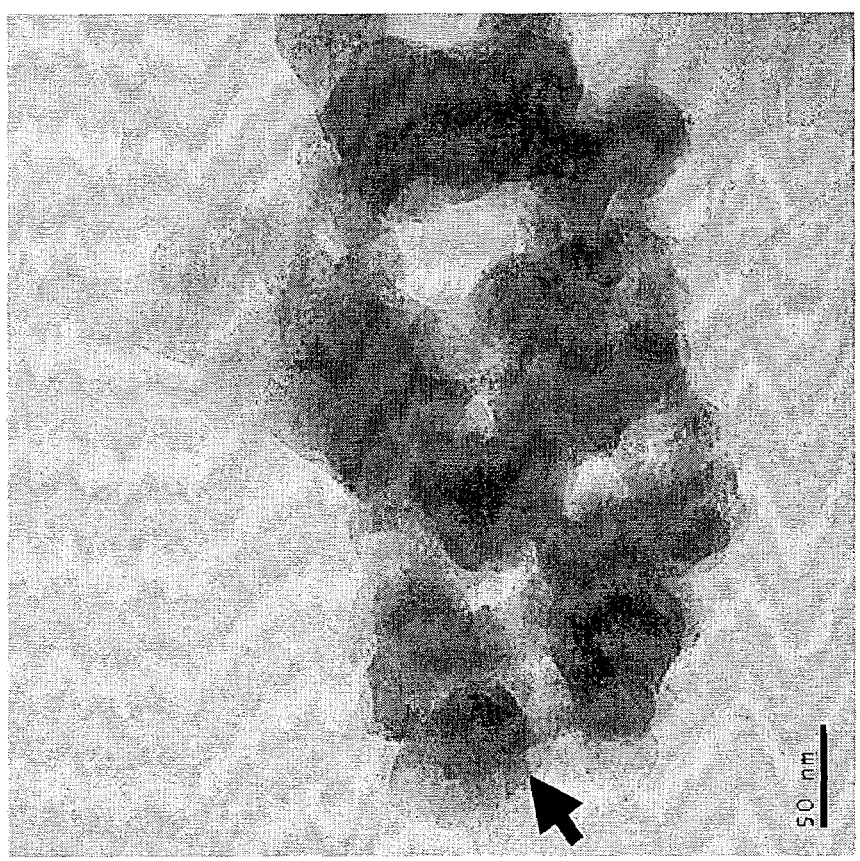

A solution of $CaCl_2$ containing 4 μg of plasmid DNA luciferase gene was then mixed with $Na_3PO_4$ solution in the presence of HEPES buffer and the reaction was allowed to take place for 15 minutes. The mixture was then added to the Osteoprogenitor cells-1 (OPC-1) (any cells could be used, OPC-1 cells were available) and allowed to incubate for either 4 or 12 hours at a pH of 7.5. (in vitro cell assays). The spherical crystals of the nanocrystalline hydroxyapatite are shown in FIGS. 8A, 8B and 8C.

The protocol by which the nanocrystalline hydroxyapatite complexes were formed is as follows. Stock reagent solutions were first prepared, including: 2 M calcium solution (2.22 g of $CaCl_2$ in 10 ml sterile water), and 2×HEPES-Buffered Saline (280 mM NaCl, 10 mM KCl, 1.5 mM $Na_3PO_4$, 12 mM dextrose, 50 mM HEPES pH 7.5).

OPC1 cells were plated the day before the transfection in 6 well plates (9.4 cm$^2$). Approximately 4×10$^5$ cell were plated in each well (cells were counted with a hemocytometer) with MEM-F12 with 10% FBS and 1% P/S. The cells were 60–70% confluent the day of transfection. The cell growth media was is changed one hour before the transfection reagent was added to media.

The transfection medium was prepared as follows (per well of a standard six well plate). Solution A contained 4 μg of plasmid DNA (pGL3: Promega), 12.4 μl 2 M calcium Solution (2.44×10$^{-5}$ moles) and sterile water up to 100 μl total. Solution B contained 100 ul of 2×HEPES Buffered Saline at pH 7.5 (1.5×10$^{-7}$ moles of phosphate). Solution A was added to Solution B dropwise while vortexing and the mixture was incubated for 20 minutes at room temperature (~25° C., no cloudiness seen). The mixture then was added dropwise into media with cells, 200 μl total per well and the cells were incubated in the presence of the transfection mixture for either 4 or 12 hours. The cells then were washed several times with PBS and fresh media was put on the cells. After washing, the cells were incubated for 2 days at 37° C. in a $CO_2$ incubator. Cells were lysed and luciferase activity was measured in a luminometer. Control calcium phosphate transfections were conducted using Clontech's CalPhos Mammalian Transfection Kit (standard protocol) using 4 μg of the same plasmid DNA used with the nanocrystalline hydroxyapatite synthesized using the method described herein.

Plasmid DNA Binding to NanoCaPs

Figure 9:
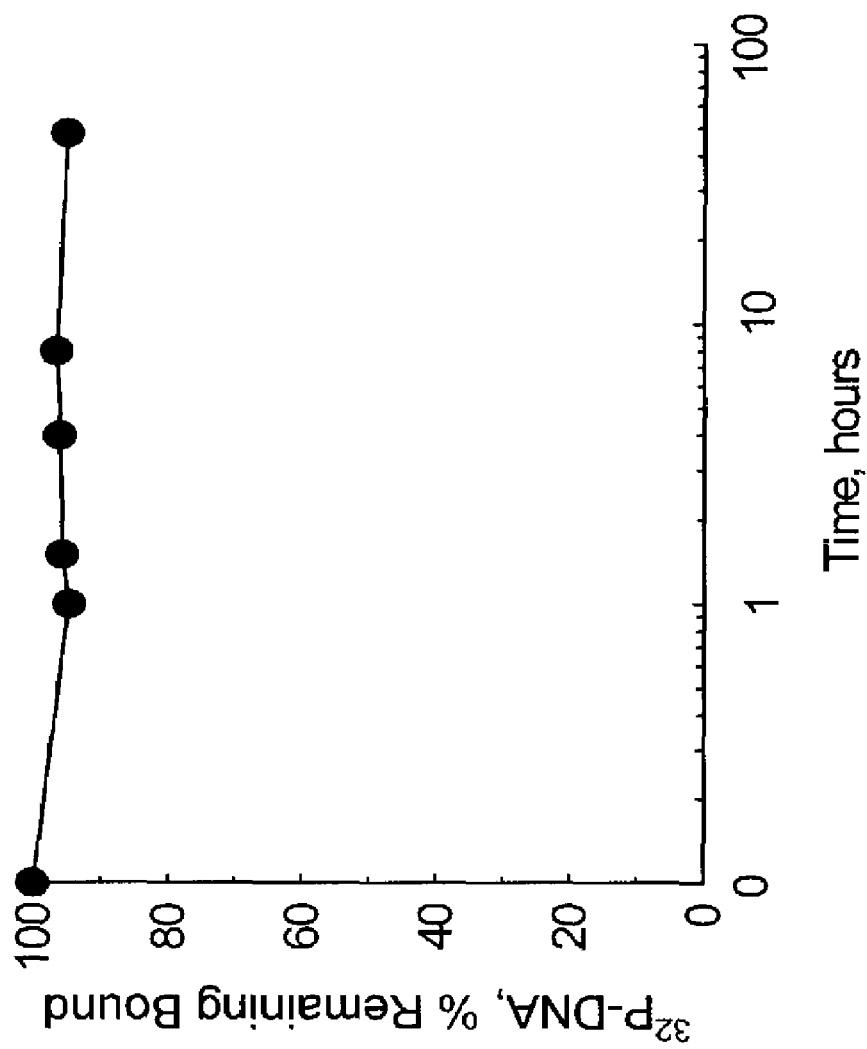
FIG. 9 is a graph showing amount of $^{32}$P-DNA retained to the hydroxyapatite as a function of time.

Retention of $^{32}$P-Luciferase DNA bound to nanocrystalline hydroxyapatite. $^{32}$P-LuciferaseDNA (~1 μg) was bound to 50 μl of an 1:40 dilution (w:v) nanocrystalline hydroxyapatite, for 45 minutes at 23° C. Bound DNA (DNA that pellets when spun briefly in a microcentrifuge, unbound DNA remains in the supernatant) was incubated under simulated in vivo conditions, 10% serum media, 37° C., with agitation. Fifty μl of incubation media was sampled at indicated time points and percentage of DNA remaining bound was determined. Results are shown in FIG. 9. The DNA was labeled with $^{32}$P using the Rediprime II DNA Labelling System from Amersham Biosciences.

In vitro Transfection Efficiency Experiment without Polymers

Figure 10A:
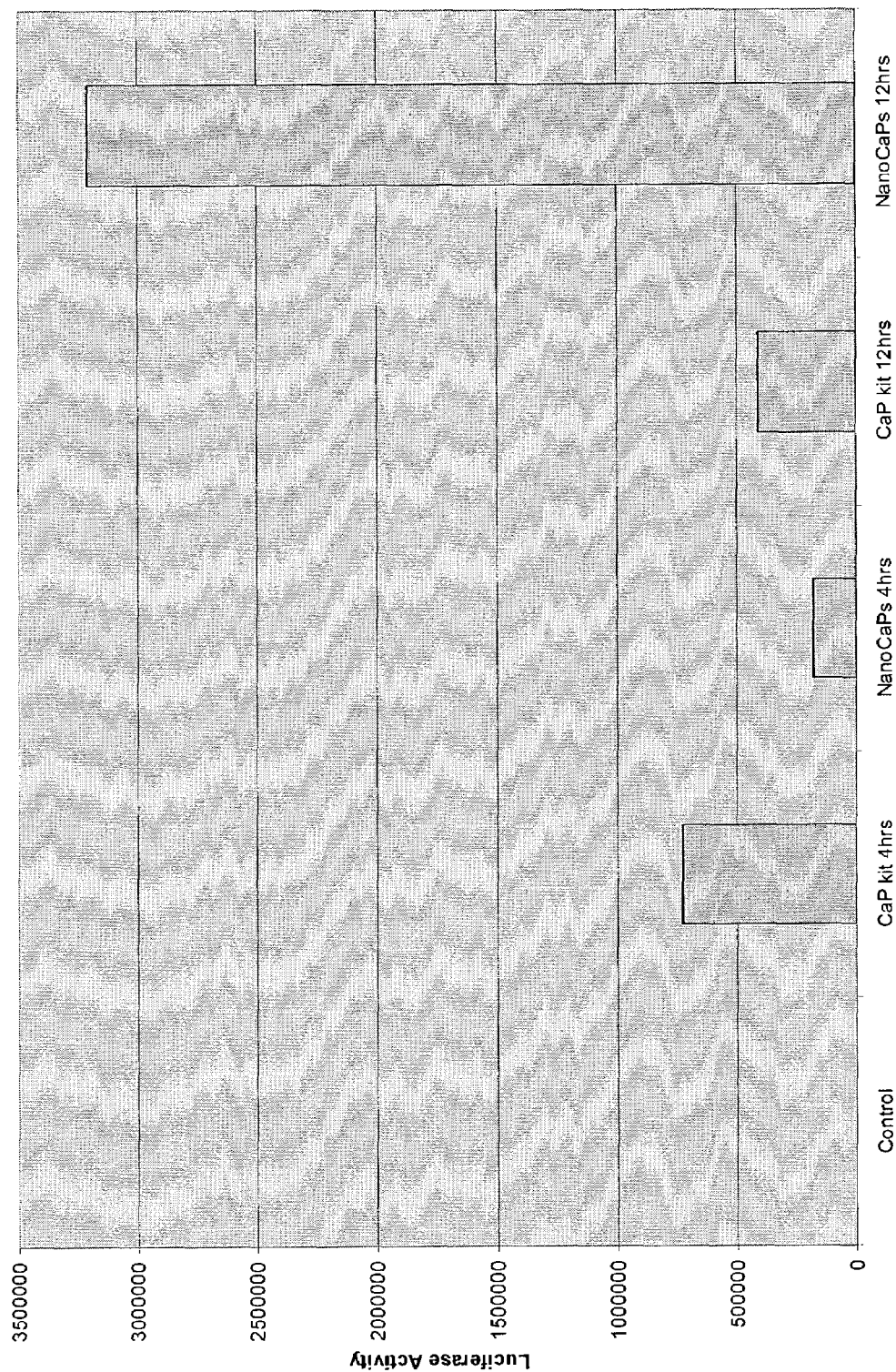
FIGS. 10A and 10B are graphs comparing transformation efficiency of the nanocrystalline hydroxyapatite particles described herein as compared to a commercially-available kit.
Figure 10B:
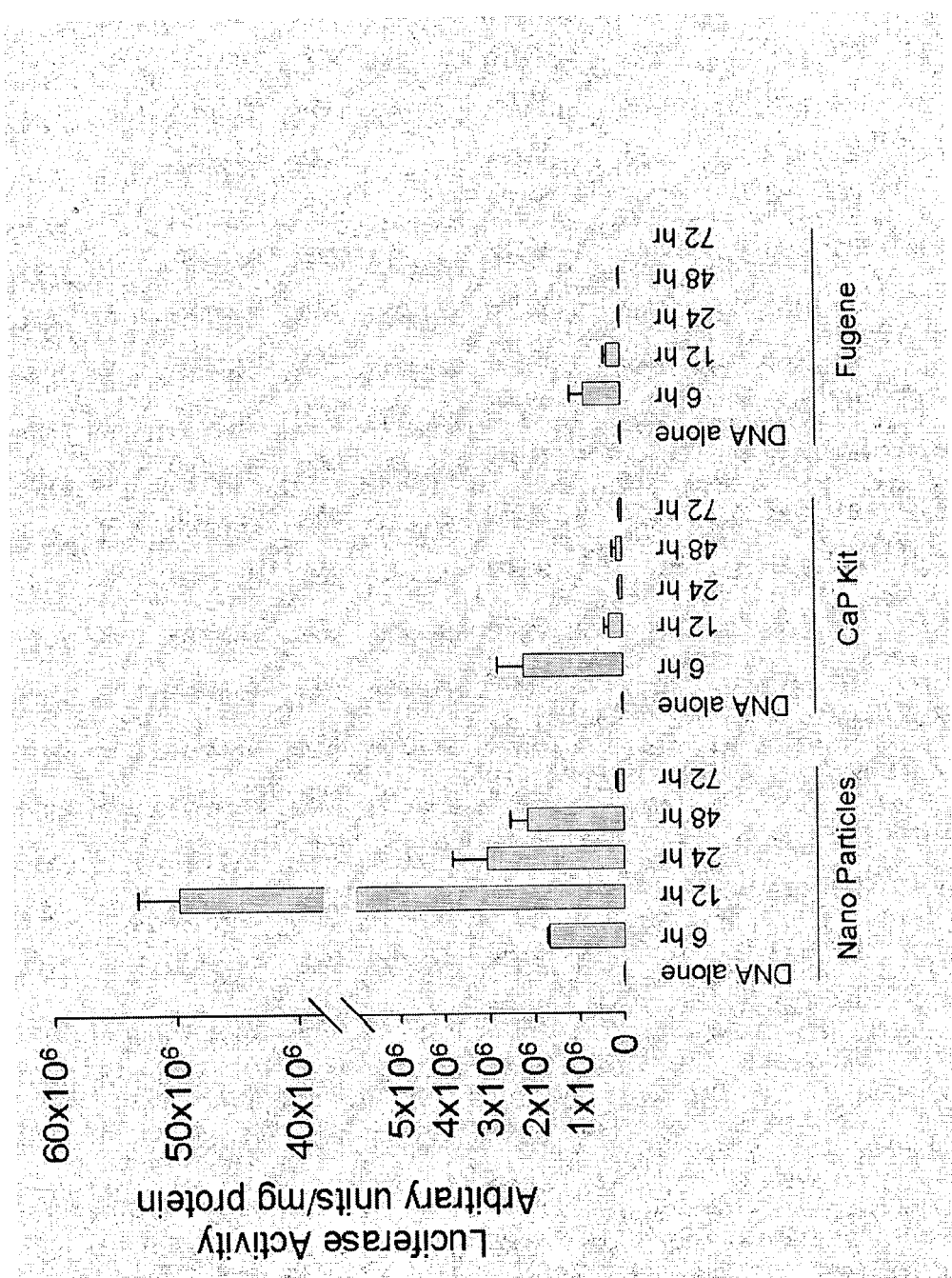

DNA-containing nanocrystalline hydroxyapatite was prepared according to the detailed protocol, provided above. This mixture was then added to the OPC-1 cells and incubated for either 4 or 12 hours at a pH of 7.5. The cells were harvested and processed using the Luciferase Assay System from Promega, substantially as provided in Promega Technical Bulletin No. 281, Revised 5/00, entitled "Luciferase Assay System" and a standard luminometer (EGG Berthold Auto Lumat LB953) was used to determine the Luciferase activity. Results are shown in FIG. 10A. This experiment was repeated using MG63 cells, further including the FUGENE, lipid-based, non-liposomal transfection kit (Roche Applied Science, Indianapolis, Ind.). Transfections were performed for 6, 12, 24, 48 and 72 hours, as shown in Figure 10B.

In vitro Transfection Efficiency Experiment with Polymers

Figure 11A:
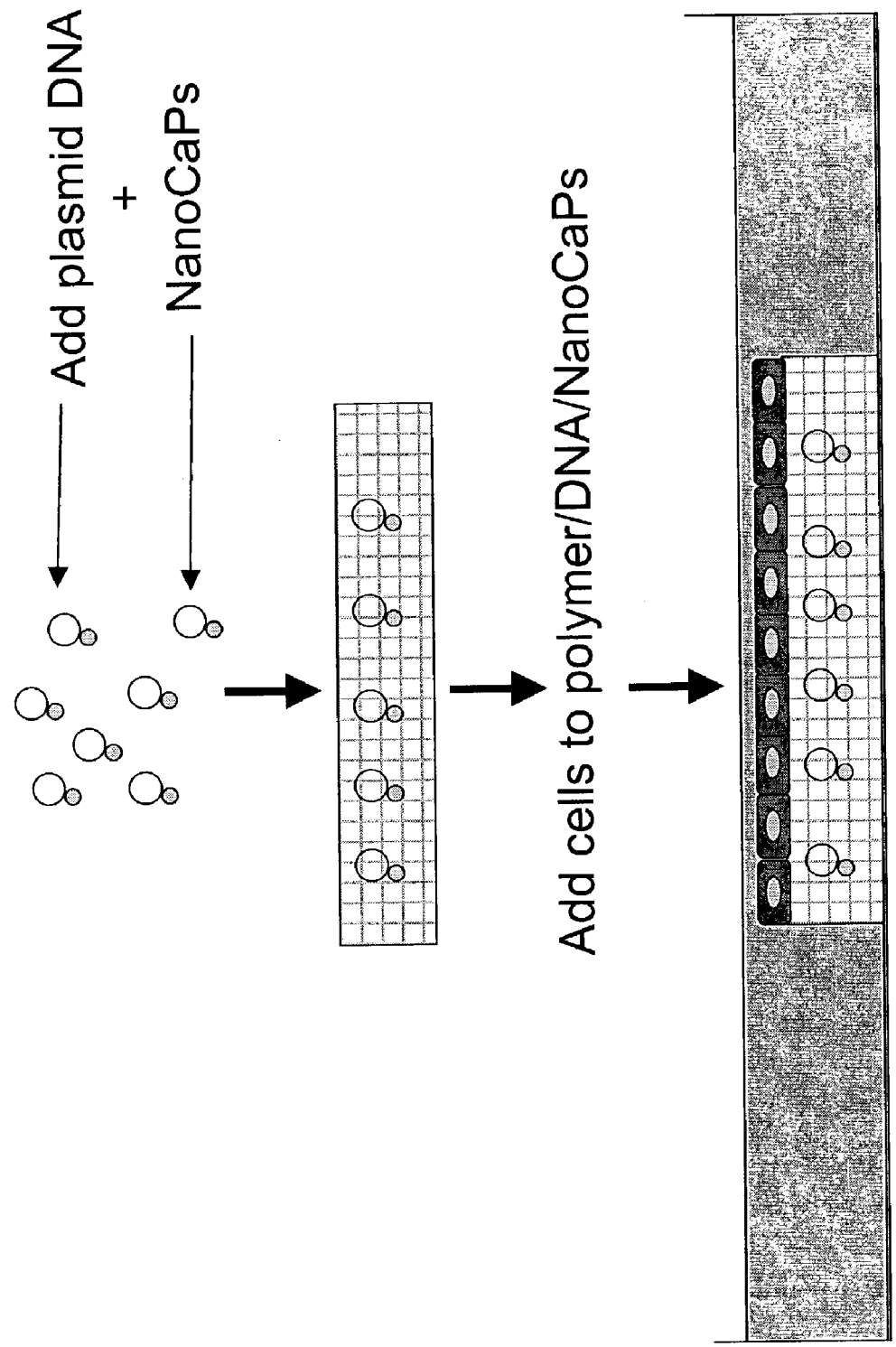
FIG. 11A is a schematic diagram illustrating an in vitro or ex vivo method for transforming cells.
Figure 11B:
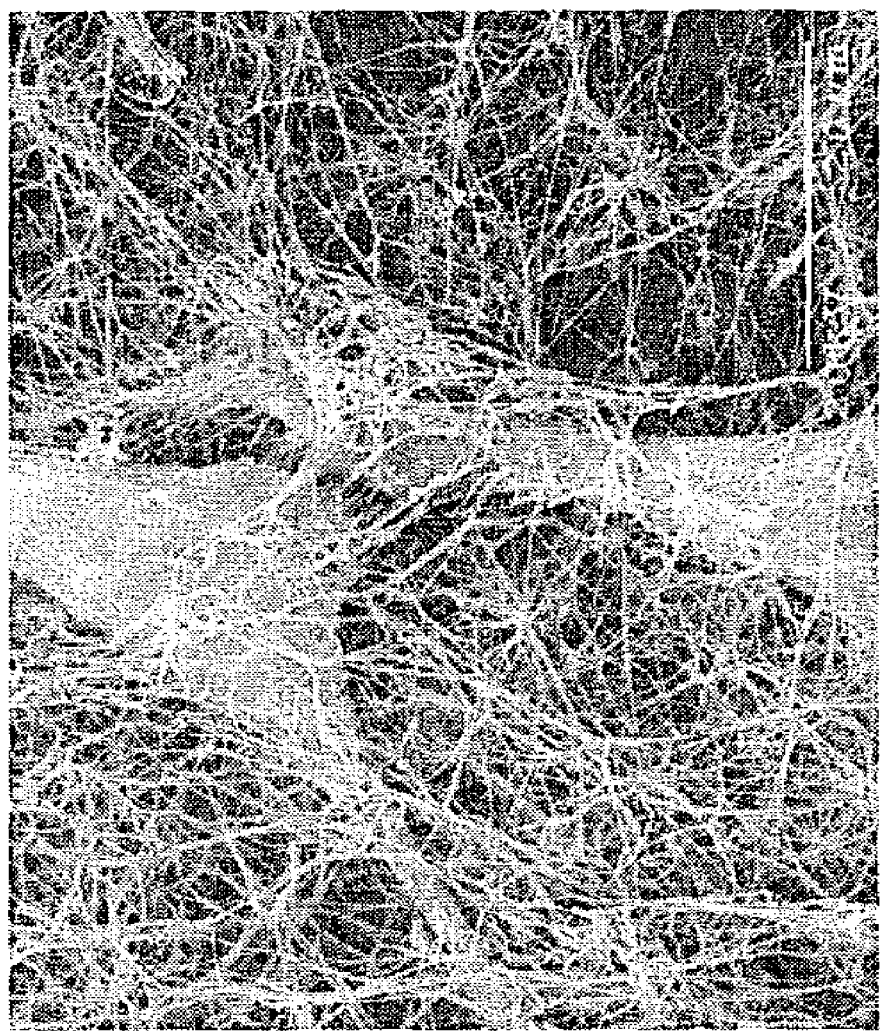
FIG. 11B is a SEM micrograph of cells treated according to the method shown in FIG. 11A.
Figure 12A:
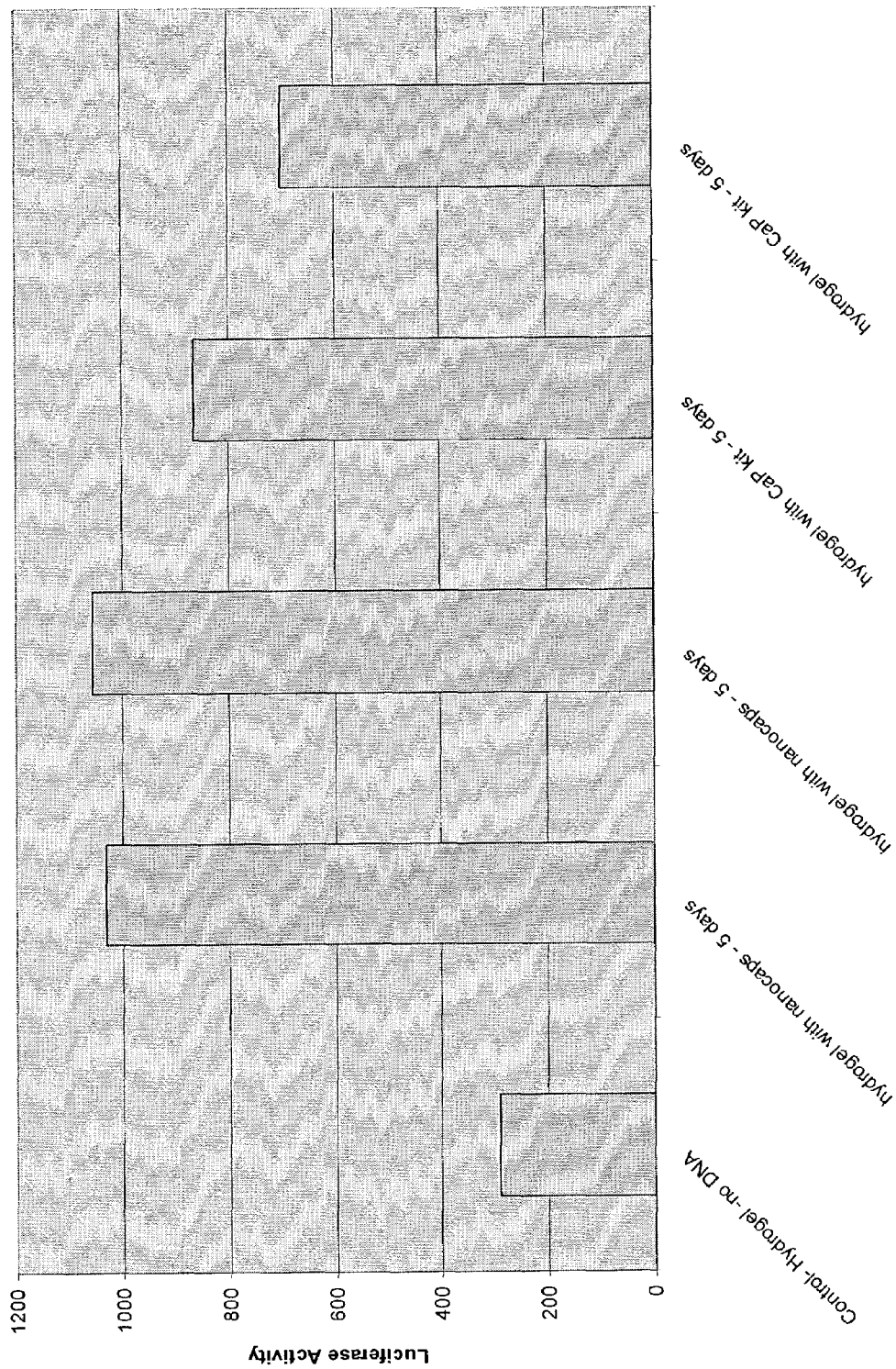
FIGS. 12A and 12B compare transformation efficiency of the polymer-associated nanocrystalline hydroxyapatite particles described herein as compared to a commercially-available kit in an embodiment of the system shown in FIGS. 11A and 11B.
Figure 12B:
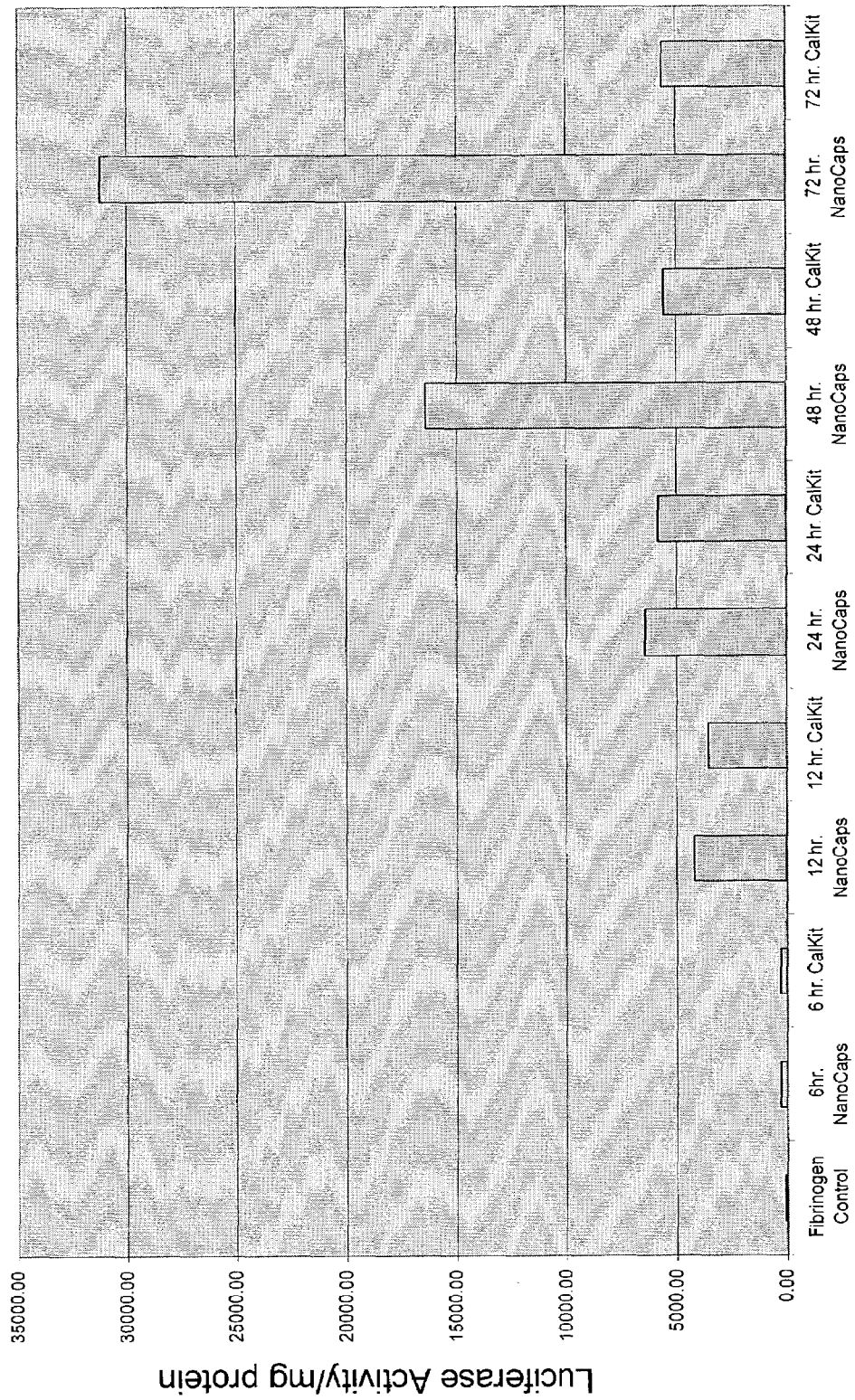

In a related experiment, nanocrystalline hydroxyapatite complexed with luciferase plasmid DNA was prepared as described above. These nanocrystalline hydroxyapatite particles were embedded in a hydrogel matrix as shown schematically in FIG. 11A and by electron micrograph in FIG. 11B. As a control, DNA was incorporated into calcium phosphate particles obtained from commercially-available methods and the particles were embedded in a hydrogel matrix in the same manner as the nanocrystalline hydroxyapatite particles. Cells were deposited onto the matrix and incubated for 5 days at which point luciferase activity was determined as shown above. Results are shown in FIG. 12A. The experiment was repeated using MG63 cells, with incubation periods of 6, 12, 24, 48 and 72 hours. Results are shown in FIG. 12B. These data indicate that the nanocrystalline hydroxyapatite particles would enhance transfection efficiency for tissue engineering application. Any other non-toxic hydrogel would be suitable for use as a matrix into which the nanocrystalline hydroxyapatite particles can be embedded.

EXAMPLE 3

Treatment of Carious Lesions by Gene Therapy

It is believed that gene delivery of growth factor(s) into the injured site may limit the inflammatory response, accelerate tissue regeneration and lead to the deposition of mineralized dentin of physiological quality.

The pulp injury model described herein is a well-established model and has been used extensively by many investigators (Hu, C. C., et al., "Reparative dentin formation in rat molars after direct pulp capping with growth factors," *J. Endod.*, (1998) 24(11):744–51; Rutherford, B., "Dentin regeneration," *Adv. Dent. Res.*, (1995) 9(3 Suppl):14; Rutherford, R. B., et al., "The time-course of the induction of reparative dentine formation in monkeys by recombinant human osteogenic protein-1," *Arch. Oral Biol.*, (1994) 39(10):833–8; Imai, M., et al., "Ultrastructure of wound healing following direct pulp capping with calcium-beta-glycerophosphate (Ca-BGP)," *J. Oral Pathol. Med.*, (1993) 22(9):411–7 and Heys, D. R., et al., "Healing of primate dental pulps capped with Teflon," *Oral Surg. Oral Med. Oral Pathol.*, (1990) 69(2):227–37.). As reviewed by Rutherford, et al. (Rutherford, B., et al., "A new biological approach to vital pulp therapy," *Crit. Rev. Oral Biol. Med.*, (1995) 6(3):218–29), most studies in this area have focused on the preservation of pulp vitality and stimulation of tertiary dentin matrices as simultaneously occurring biological phenomena. The repair or regeneration of pulp tissue is usually considered in combination with dentinogenesis and not as a therapeutic goal unto itself. This is a logical extension of the concept of the dentin-pulp complex as an integral structural and functional unit. The approach outlined below applies tissue engineering principles for dentin regeneration. The goal is to provide a matrix, such as a fibrin matrix, that would be replaced by invading cells which will uptake pDNA bound to the nanocrystalline calcium phosphate particles and thus differentiate into a specialized connective tissue that is subsequently mineralized. This reparative dentin forms superficial to the pulp tissue, and not at the expense of the pulp tissue.

Figure 13:
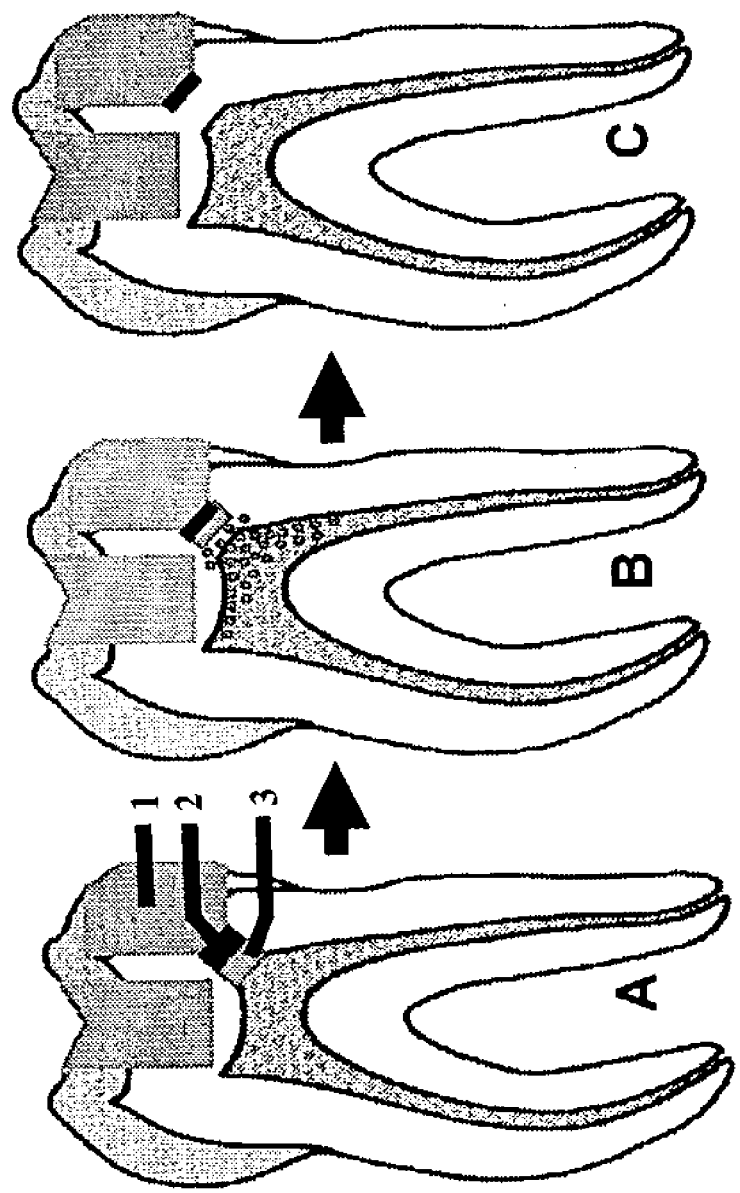
FIG. 13 depicts schematically repair of a tooth as described in Example 3.

In detail, the rats will be heavily sedated and the operating field will be disinfected with 5% solution of iodine. The pulps will be exposed using a sterile high-speed rotary cutting instruments with water coolant. Partial hemostasis will be achieved with sterile cotton pellets but the teeth will not be dried extensively before treatment. The pulps will be treated with fibrin matrix containing the nanocrystalline calcium phosphate particles/pDNA of interest (FIG. 13, step 1, area 3). This will be followed by the application of a biodegradable self-setting cement to seal the injured pulp and insulate the site from the final restorative material (FIG. 13, step 1, area 2). The fibrin matrix will release the pDNA to migrating pulp cells allowing them to uptake the plasmid DNA (FIG. 13, step B). The teeth will then be sealed with a sealant, such as Temp-Bond NE (Kerr U.S.A., Romulus, Mich., U.S.A.) (FIG. 13, step 1, area 1). The goal of this therapy is to induce dentin regeneration and the formation of a dentin bridge to maintain a healthy pulp (FIG. 13, step C). The approach is based on exploiting the existing model used by clinicians but also implements dentin gene therapy, which will lead to significant benefits to patients suffering from dental caries.

In the described procedure, the delivered gene is preferably an OP1 gene, such as BMP-2, -4 or -7. The logic for selecting BMP-7 is based on biology and literature. Recent evidence has implicated proteins belonging to the bone morphogenetic protein (BMP) subgroup of the transforming growth factor beta supergene family in tooth formation and dentinogenesis. It has long been known that bone and dentin contain bone morphogenetic protein activity. Recombinant human BMP-2, -4, and -7 have been shown to induce reparative dentin formation in experimental models of large direct pulp exposures in permanent teeth (Rutherford, B., (1995); Begue-Kim, C., et al., "Effects of dentin proteins, transforming growth factor beta 1 (TGF beta 1) and bone morphogenetic protein 2 (BMP2) on the differentiation of odontoblast in vitro," *Int. J. Dev. Biol.*, (1992) 36(4):491–503; Ren, W. H., et al., "Induction of reparative dentin formation in dogs with combined recombinant human bone morphogenetic protein 2 and fibrin sealant," *Chin. J. Dent. Res.*, (1999) 2(3–4):21–4 and Nakashima, M., "The induction of reparative dentine in the amputated dental pulp of the dog by bone morphogenetic protein," *Arch. Oral Biol.*, (1990) 35(7):493–7). BMP-7 has documented potential for successful dentin regeneration and is a well-established model therefor.

The rat BMP-7 plasmid DNA may be controlled by the CMV promoter 5' to the coding region as described by Krebsbach, P. H., et al. "Gene therapy-directed osteogenesis: Bmp-7-transduced human fibroblasts form bone in vivo," *Hum Gene Ther* 2000; 11: 1201–1210 and Franceschi, R. T., et al., "Gene therapy for bone formation: in vitro and in vivo osteogenic activity of an adenovirus expressing bmp7," *J Cell Biochem* 2000; 78: 476–486.

EXAMPLE 4

Ectopic Gene Delivery of BMP-2 in Rat Muscle Wound Model

In the experiments described below, the well-established ectopic wound model was selected. The gene encoding BMP-2 was selected as a known bone inducing agent. Several authors (Whang, K., et al., "Ectopic bone formation via rhBMP-2 delivery from porous bioabsorbable polymer scaffolds," *J. Biomed. Mater. Res.*, (1998) 42(4): 491–9; Uludag, H., et al., "Characterization of rhBMP-2 pharmacokinetics implanted with biomaterial carriers in the rat ectopic model," *J. Biomed. Mater. Res.*, (1999) 46(2):193–202; Uludag, H., et al., "Implantation of recombinant human bone morphogenetic proteins with biomaterial carriers: A correlation between protein pharmacokinetics and osteoinduction in the rat ectopic model," *J. Biomed. Mater. Res.*, (2000) 50(2): 227–38; Urist, M. R., "Bone: formation by autoinduction," *Science*, (1965) 150(698): 893–9 and Ogawa, Y., et al., "Bovine bone activin enhances bone morphogenetic protein-induced ectopic bone formation," *J. Biol. Chem.*, (1992) 267(20):14233–7) have demonstrated that a matrix containing rhBMP-2 implanted in an ectopic site will induce bone formation.

To demonstrate bone formation using a hydroxyapatite complex as described herein, nanocrystalline hydroxyapatite particles complexed with plasmid DNA harboring a BMP-2 gene (see, generally, Lee, J. Y., et al. "Enhancement of bone healing based on ex vivo gene therapy using human muscle-derived cells expressing bone morphogenetic protein 2," *Hum Gene Ther*. 2002 Jul. 1; 13(10):1201–11; Nobuhiro Abe, et al., Enhancement of bone repair with a helper-dependent adenoviral transfer of bone morphogenetic protein-2, I 2002 Sep. 27; 297(3):523–7; and Laurencin, C. T. et al., "Poly(lactide-co-glycolide)/hydroxyapatite delivery of BMP-2-producing cells: a regional gene therapy approach to bone regeneration," *Biomaterials*. 2001 Jun.; 22(11): 1271–7) under transcriptional control of the CMV promoter were embedded in a fibrin matrix and tested in vivo according to the following.

Matrix preparation: sterile stock solution of fibrinogen (45.63 mg/ml) was prepared using sterile PBS solution. BMP-2 plasmid DNA was lyophilized and mixed with the nanocrystalline hydroxyapatite prepared as described above. The hydroxyapatite/DNA complex was added to a stock solution of thrombin 5 U/ml in PBS and the hydroxyapatite/DNA complex/thrombin was added to and mixed with the fibrinogen stock solution rapidly poured into 1 ml sterile syringes with their tops removed to form gel plugs. The gel plugs were implanted in the hind lateral muscle site of adult female Sprague-Dawley rats. The surgical protocol consists of a single 2–3 cm incision in the lateral aspect of the hind to reach the muscle structure. The plasmid DNA-nanocrystalline calcium phosphate particles incorporated in fibrin was inserted in the muscle and the wound was then closed with 4.0 sutures. The rats were euthanized 4 weeks later, x-rays of the rat leg were performed and tissues from the muscle structure were retrieved, fixed in formalin, and embedded in paraffin. Serial histological sections were prepared and stained with Masson's Trichrome to determine bone formation.

Figure 14B:
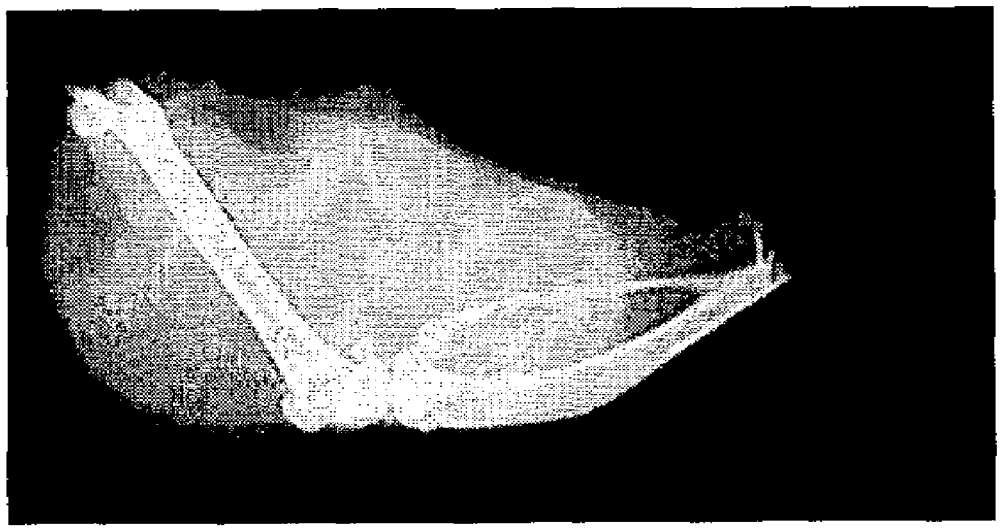
FIGS. 14A and 14B show x-rays of fibrin matrix containing the nanocrystalline hydroxyapatite particles described herein both with (14A) and without (14B) plasmid DNA implanted into the mouse hind limb muscle.
Figure 14A:
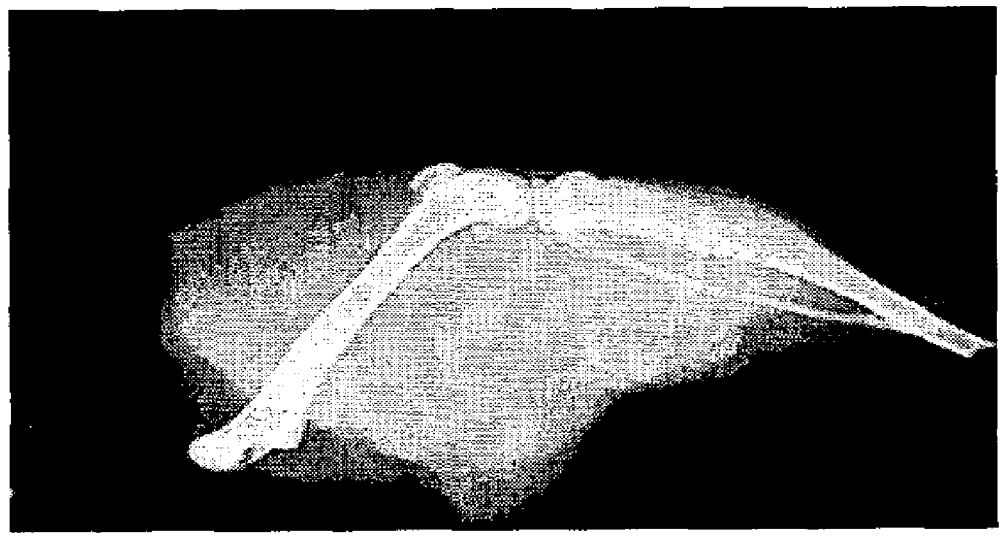
Figure 15A:
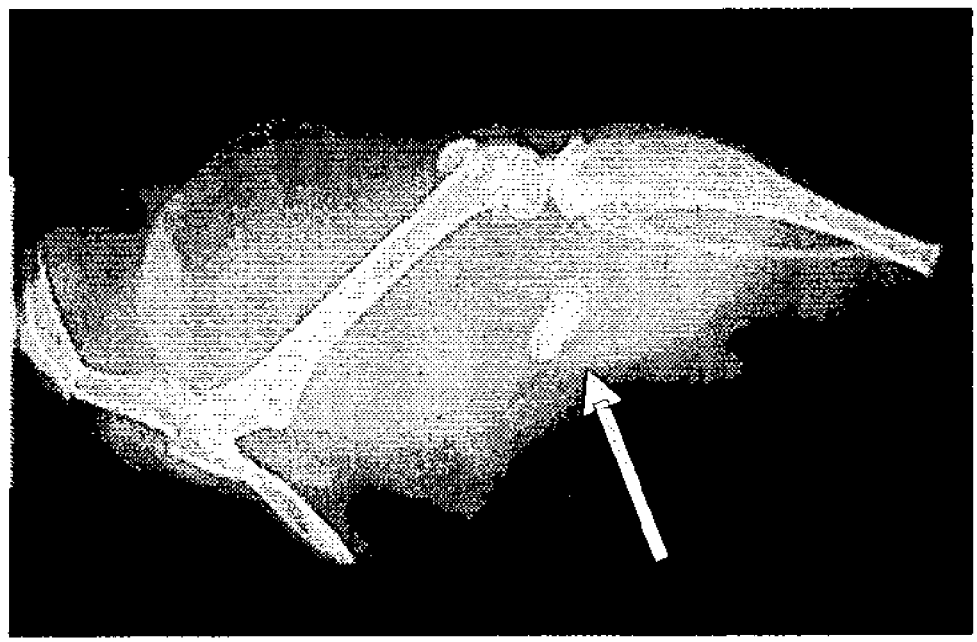
FIGS. 15A and 15B show x-rays of fibrin matrix containing hydroxyapatite complexes with pBMP-2 (encoding for the recombinant human Bone Morphogenetic Protein-2 (rh-BMP-2)) implanted into the mouse hind limb muscle.
Figure 15B:
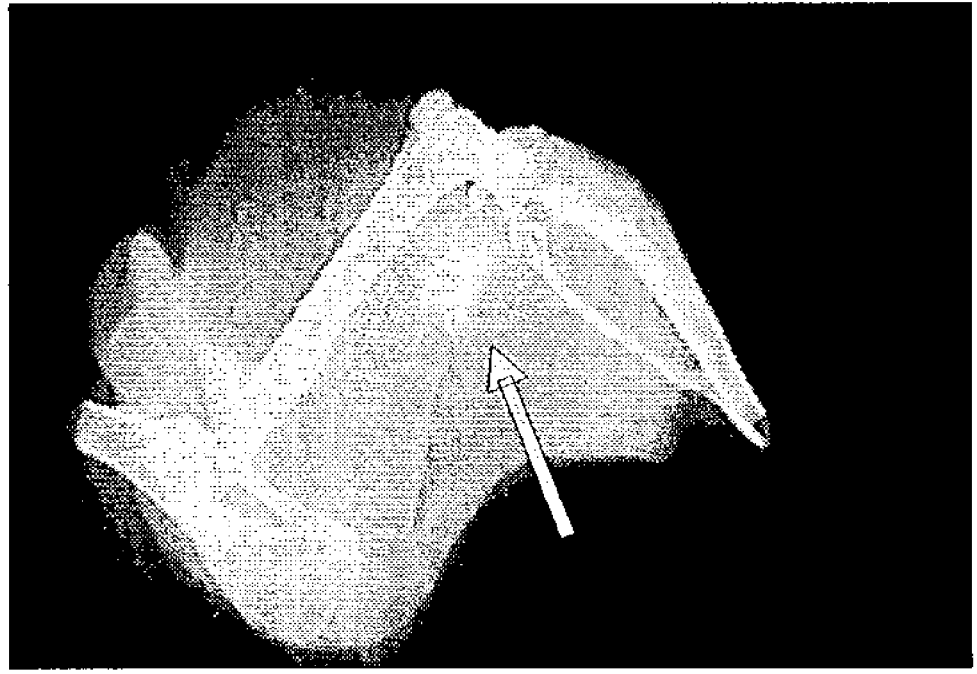

These studies show the formation of a radio dense structure following x-ray imaging when 500 μg of plasmid BMP-2/Nanocrystalline calcium phosphate particles were incorporated into a fibrin matrix and implanted into a rat muscle (FIGS. 15A and 15B). The controls (FIGS. 14A and 14B) using fibrin/nanocrystalline calcium phosphate particles without plasmid DNA did not show any radio dense structures. The results of these studies provide an indication that the pDNA was indeed uptaken and expressed by the cells in vivo.

EXAMPLE 5

Method for Synthesizing Membranes

The protocol described for synthesizing nanostructured calcium phosphate can also be used for synthesizing membranes. A typical protocol will include the steps of adding the $CaCl_2$ solution containing plasmid DNA to the $Na_3PO_4$ solution in the presence of a water soluble polymer such as polyethylene glycol or PMMA. The resulting mixture can then be air-dried or dried in vacuum to generate the polymeric structure containing the nanosized hydroxyapatite particles. The thickness of the membrane can be adjusted by controlling the viscosity of the mixture which will essentially depend on the concentration of the polymer and the water. The resulting solution of appropriate viscosity can then be poured onto a Teflon substrate to form membranes of different thicknesses. A porous membrane structure can be generated by bubbling air or oxygen into the mixture containing the phosphate and the polymer. The gas droplets trapped in the viscous mixture will help generate the porosities resulting in a porous structure. Alternatively the porogen can be a material that is not water soluble such as poly-ε-caprolactone which can then be removed by adding tetrahydrofuran. The porosity and pore sizes can be controlled by the amount of the pore former and the size of the polymer beads.

EXAMPLE 6

Method for Synthesizing Pastes, Creams or Gels

Any method described in the prior-art for manufacturing of creams or pastes or gels can be used for generating the same with nanosized calcium phosphates. A typical procedure would consist of adding the $CaCl_2$ solution containing plasmid DNA to the $Na_3PO_4$ solution to a mixture containing ingredients, such as polyethylene glycol, mineral oil, isopropyl myristate, sorbitan peroleate, glyceryl lanolate, sorbitol, cetyl palmitate, magnesium sulfate, aluminum stearate, lanolin, alcohol, and ampiphilic surfactants such as laurel sulfate ester or sodium dodecyl sulfate. These are components of several commercial creams, pastes and gels used for cosmetic applications. The addition of the hydroxyapatite solutions into these mixtures containing the ampiphiles will result in micellar structures of the nanocap within the gel structures. Application on a surface will help in dissolving the structures providing easy application and transfer of the hydroxyapatite particles or complexes into the skin.

EXAMPLE 7

Method for Synthesizing Solutions for Ocular Applications

The protocol for this application typically includes the steps of adding solution containing $CaCl_2$ and plasmid DNA to the solution containing $Na_3PO_4$. Additional additives such as PEG or EDTA could be added as well as any other biodegradable water soluble polymer which, for example, can serve as steric stabilizers or complexing agents to prevent aggregation of the hydroxyapatite particles or complexes. The resulting solution can be added to a saline mixture which can then be easily dispensed into the eye for ocular applications. The amounts of the additives and the concentration of the hydroxyapatite particles and the plasmid DNA can be optimized depending on the use and type of therapy.

EXAMPLE 8

Method for Synthesizing Aerosols for Respiratory Applications

The protocol for this application is essentially very similar to Example 6, except that a mist or aerosol droplets of the resulting stabilized solution containing PEG or EDTA or any water soluble biodegradable polymer will generated using an ultrasonic transducer or like devices. In a typical aerosol applicator the solution can be pressurized through an orifice to generate a mist of extremely fine droplets of the hydroxyapatite particles or complexes-containing solution. The size of the droplets and the concentration of the complexes containing the DNA or other bioactive compound in each droplet can be controlled depending on the therapy and application site.

EXAMPLE 9

Method for Synthesizing Substrates Containing the Nano-sized Calcium Phosphates.

The above methods also can be used for coating a number of metal, ceramic, and semiconducting substrates for applications ranging from stents to hard and soft tissue implants. In a typical protocol, a solution containing $CaCl_2$ and plasmid DNA will be added to a solution containing the $Na_3PO_4$ to produce hydroxyapatite. The resulting solution can be stabilized with PEG, EDTA or any biodegradable polymer. The substrates can be, for example and without limitation metallic, ceramic or semiconducting materials such as Ti—V—Al, Co—Cr, Co—Mo alloys and SiC, semiconducting grade silicon, or silica, and carbon forms including amorphous pyrolytic graphite and nanotubes. Silicon carbide (SiC) or silica ($SiO_2$) can be made porous on the surface by surface etching techniques either chemical or bombardment by surface active ions in a sputtering unit. The substrates containing porosities on the surface will then be dipped into the solution mix containing the plasmid DNA and the nanosized calcium phosphates. The coated solution will then be dried and can be used for the desired application. The concentration of the DNA and the hydroxyapatite and the porosity on the surface all can be controlled and optimized depending on the application, the site of use in the body and the therapy. Similar procedures can be applicable to ceramic or metal fibers and porous membranes of metal, ceramics or semiconductors including carbon nanotubes.

We claim:

1. A method for making nanocrystalline hydroxyapatite, comprising the step of reacting calcium ions with phosphate ions in the presence of hydroxyl ions to form calciumphosphate, wherein the ratio of calcium ions to phosphate ions in the reaction is greater than 167.

2. The method of claim 1, wherein the reacting step comprises the step of mixing a calcium ion-containing solution with a solution comprising trisodium phosphate.

3. The method of claim 1, wherein the reacting step comprises the step of mixing a calcium chloride solution with a solution containing phosphate ions.

4. The method of claim 1, wherein the calcium phosphate is precipitated in the presence of a biomolecule.

5. The method of claim 4, wherein the biomolecule is a nucleic acid.

6. The method of claim 4, wherein the biomolecule is DNA.

7. The method of claim 6, wherein the DNA comprises a bone morphogenetic protein gene.

8. The method of claim 6, wherein the DNA comprises a gene slected from the group consisting of rhBMP-2, VEGF, EGF, NGF, TGF-β, FGF, PDGF, IGF, Runx2, Osx and BMP-7.

9. The method of claim 6, wherein the DNA comprises a gene.

10. The method of claim 4, wherein the biomolecule is plasmid DNA.

11. The method of claim 4, wherein the biomolecule is RNA.

12. The method of claim 11, wherein the RNA is one of an antisense RNA and an interfering RNA.

13. The method of claim 1, further comprising the step of associating the calcium phosphate with a substrate.

14. The method of claim 13, wherein the substrate is a polymer matrix.

15. The method of claim 14, wherein the polymer matrix comprises a natural polymer.

16. The method of claim 15, wherein the natural polymer is selected from the group consisting of fibrin, carrageenan, chitosan, hyaluronic acid, alginate and collagen.

17. The method of claim 13, wherein the substrate is configured as a biomimetic extracellular matrix.

18. The method of claim 1, further comprising the step of depositing the calcium phosphate onto a substrate.

19. The method of claim 18, wherein the substrate is configured as a biomimetic extracellular matrix.

20. The method of claim 18, wherein the substrate is a polymer.

21. The method of claim 1, further comprising the step of incorporating the calcium phosphate into a pharmaceutically acceptable dosage form.

22. The method of claim 21, wherein the dosage form is a transdermal form.

23. The method of claim 21, wherein the dosage form is an aerosol form.

24. The method of claim 21, wherein the dosage form is a parenteral form.

25. The method of claim 21, wherein the dosage form is an oral form.

26. A method for introducing a biomolecule into a cell, comprising the step of contacting a cell with a composition comprising nanocrystalline hydroxyapatite prepared according to the step of reacting calcium ions with phosphate ions in the presence of a biomolecule and hydroxyl ions, at a calcium ion to phosphate ion ratio of greater than 167.

27. The method of claim 26, wherein the hydroxyapatite is prepared according to the formula:

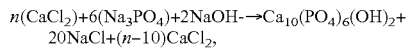

wherein n is greater than 10.

28. The method of claim 27, wherein the biomolecule is DNA.

29. The method of claim 28, wherein the DNA contains a gene.

30. The method of claim 28, wherein the DNA comprises a bone morphogenetic protein gene.

31. The method of claim 28, wherein the DNA comprises a gene selected from the group consisting of rhBMP-2, VEGF, EGF, NGF, TGF-β, FGF, PDGF, IGF, Runx2, Osx and BMP-7.

32. A method for treating a bone or tooth injury comprising the step of introducing into a site of injury in a bone or tooth a matrix containing a nanocrystailine hydroxyapatite complex comprising the nanocrystalli ne hyd roxyapatite complexed with a biomaterial, wherein the nanocrystalline hydroxyapatite is prepared by reacting calcium ions with phosphate ions in the presence of hydroxyl ions, wherein the ratio of calcium ions to phosphate ions is greater than 167.

33. A method for making hydroxyapatite comprising the step of reacting calcium ions with phoshate ions in the presence of hydroxyl ions, wherein the ratio of calcium ions to phosnhate ions is greater than 1.67 wherein the hydroxyapatite is prepared accord ing to the formula:

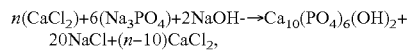

wherein n is greater than 10, and further wherein the hdroxyapatite is precipitated by mixing a solution of calcium chloride with a solution of NaCl, KCl, $Na_3PO_4$, and a buffer adjusted to pH 7.5 with NaOH, wherein the solution of NaCl, KCl, $Na_3PO_4$ and a buffer adjusted to pH 7.5 with NaOH, additionally comprises a sugar.

34. The method of claim 33, wherein the hydroxyapatite is precipitated by mixing a solution of calcium chloride with a solution of about 280 mM NaCl about 10 mM KCl, about 1.5 mM $Na_3PO_4$, and about 50 mM HEPES adjusted to pH 7.5 with NaOH, wherein the solution of about 280 mM NaCl, about 10 mM KCl, about 1.5 mM $Na_3PO_4$ and about 50 mM HEPES adjusted to pH 7.5 with NaOH, additionally comprises about 12 mM dextrose.

* * * * *

UNITED STATES PATENT AND TRADEMARK OFFICE
CERTIFICATE OF CORRECTION

PATENT NO. : 7,247,288 B2
APPLICATION NO. : 10/393507
DATED : July 24, 2007
INVENTOR(S) : Kumta et al.

It is certified that error appears in the above-identified patent and that said Letters Patent is hereby corrected as shown below:

Column 2, line 52, delete "Marra, KG" and insert --Marra, K.G.-- therefor.

Column 3, line 6, delete "Fang, J., et aL," and insert --Fang, J., et al.-- therefor.

Column 8, line 15, delete "$n(CaCl_2) + (Na_3PO_4) + \geqq$" and insert
-- $n(CaCl_2) + (Na_3PO_4) + \geq$ -- therefor.

Column 24, line 4, delete "form calciumphosphate" and insert --form calcium phosphate-- therefor.

Column 25, line 19, delete "a na nocystailine" and insert --a nanocystalline-- therefor.

Column 25, line 20, delete "the nanocystalli ne hy droxyapite" and insert --the nanocystalline hydroxyapatite.-- therefor.

Signed and Sealed this

Fifth Day of February, 2008

JON W. DUDAS
*Director of the United States Patent and Trademark Office*